(12) United States Patent
Aoki et al.

(10) Patent No.: US 9,089,183 B2
(45) Date of Patent: Jul. 28, 2015

(54) BICYCLE CLEAT POSITIONING KIT

(75) Inventors: Toshiaki Aoki, Sakai (JP); Junichi Kikuta, Sakai (JP)

(73) Assignee: Shimano Inc., Osaka (JP)

( * ) Notice: Subject to any disclaimer, the term of this patent is extended or adjusted under 35 U.S.C. 154(b) by 446 days.

(21) Appl. No.: 13/595,970

(22) Filed: Aug. 27, 2012

(65) Prior Publication Data

US 2013/0318805 A1    Dec. 5, 2013

Related U.S. Application Data

(63) Continuation-in-part of application No. 13/484,099, filed on May 30, 2012, now Pat. No. 8,984,759.

(51) Int. Cl.

| | |
|---|---|
| *G01B 1/00* | (2006.01) |
| *A43B 5/14* | (2006.01) |
| *A43D 1/08* | (2006.01) |
| *B62M 3/08* | (2006.01) |
| *A61B 5/103* | (2006.01) |
| *A61B 5/107* | (2006.01) |
| *B23Q 17/00* | (2006.01) |
| *A43D 1/02* | (2006.01) |
| *A43D 5/00* | (2006.01) |
| *A43D 5/02* | (2006.01) |

(52) U.S. Cl.
CPC ... *A43B 5/14* (2013.01); *A43D 1/08* (2013.01); *B62M 3/08* (2013.01); *B62M 3/086* (2013.01); *A43D 1/02* (2013.01); *A43D 5/00* (2013.01); *A43D 5/02* (2013.01); *A61B 5/103* (2013.01); *A61B 5/107* (2013.01); *B23Q 17/00* (2013.01); *B62K 2207/00* (2013.01); *G01B 1/00* (2013.01)

(58) Field of Classification Search
CPC ........ A61B 5/103; A61B 5/107; B23Q 17/00; A43D 1/02; A43D 1/08; A43D 5/00; A43D 5/02; A43B 5/14; B62M 3/08; B62M 3/086; G01B 1/00; B62K 2207/00
USPC ...... 33/512, 3 R, 3 A, 3 B, 36, 613, 645, 3 C; 29/407.01, 705; 12/123
See application file for complete search history.

(56) References Cited

U.S. PATENT DOCUMENTS

| | | | | |
|---|---|---|---|---|
| 2,867,362 | A * | 1/1959 | Bloch | 223/120 |
| 5,946,754 | A * | 9/1999 | Baldini | 12/123 |
| 8,196,243 | B2 * | 6/2012 | Hogg | 12/142 P |
| 2010/0307030 | A1 | 12/2010 | Tafaute et al. | |
| 2013/0333124 | A1 * | 12/2013 | Okamoto et al. | 12/123 |

FOREIGN PATENT DOCUMENTS

| | | |
|---|---|---|
| FR | 2940020 A1 | 6/2010 |
| WO | 2005/025974 A1 | 3/2005 |

OTHER PUBLICATIONS

Photograph of Mavic Ergo Cleat setting tool from http://joepapp.blogspot.com/2010/01/mavic-ergo-cleatalignment-system.html—Published Jan. 30, 2010.
Ergon Bike Ergonomics; Check you cleats; from http://www.ergon-bike.com/us/en/blog/; Feb. 2012; Ergon USA.

* cited by examiner

*Primary Examiner* — R. A. Smith
*Assistant Examiner* — Tania Courson
(74) *Attorney, Agent, or Firm* — Global IP Counselors

(57) ABSTRACT

A bicycle cleat positioning kit includes a reference indicating instrument and a cleat adjusting instrument. The reference indicating instrument includes a shoe reference indicator with respect to a bicycle shoe. The cleat adjusting instrument includes a cleat adjusting indicator indicative of an adjustment amount of a cleat with respect to the shoe reference indicator of the reference indicating instrument.

14 Claims, 33 Drawing Sheets

30L

| E | FOOT OPEN ANGLE | 6 | TEMPLATE |
|---|---|---|---|
| F | SHOES ANGLE | 2/1 | SPD-SL 2 DEG<br>SPD 1 DEG |
| G | FOOT-SHOES ANGLE | 1 | TEMPLATE |
| H | SHOES-CLEAT ANGLE | 3 | E-F-G |
| I | F/R CLEAT POSITION | -9 | TEMPLATE |
| J | IN/OUT CLEAT POSITION | 6 | TEMPLATE |
| K | PEDLING ANGLE | | THIS SHEET |
| L | PEDLING ADJUST | | THIS SHEET |
| M | F/R ADJUSTED POSITION | | I+L |
| N | CRANK ATTACH ADJUST | | THIS SHEET |
| O | ADJUSTED IN/OUT POSITION | 0 OR -4mm IN | 0 : NORMAL AXLE<br>-4 :4MM LONG AXLE |
| P | NORMAL/LONG AXLE | | J+N+O |

FIG. 15

BICYCLE CLEAT POSITIONING KIT

CROSS-REFERENCE TO RELATED APPLICATIONS

This application is a continuation-in-part application of U.S. patent application Ser. No. 13/484,099 filed on May 30, 2012. The entire disclosure of U.S. patent application Ser. No. 13/484,099 is hereby incorporated herein by reference.

BACKGROUND

1. Field of the Invention

This invention generally relates to a bicycle cleat positioning kit. More specifically, the present invention relates to a bicycle cleat positioning kit for a cleat of a bicycle shoe.

2. Background Information

Bicycling is becoming an increasingly more popular form of recreation as well as a means of transportation. Moreover, bicycling has become a very popular competitive sport for both amateurs and professionals. Whether the bicycle is used for recreation, transportation or competition, the bicycle industry is constantly improving the various components of the bicycle.

Pedals are an essential bicycle component in that they transfer cycling power to the bicycle's drive train. Different styles of bicycles utilize different bicycle pedal styles that are designed for a specific purpose such as for pleasure, off road biking, road racing, etc. In recent years, step-in or clipless pedals have gained more popularity. The step-in or clipless pedal releasably engages a cleat secured to the sole of a rider's bicycle shoe. In other words, the cleats are attached to the soles of bicycle shoes. The cleats lock the rider's feet into pedals of bicycle. More specifically, the cleats lock the rider's feet position and the rider's feet angle with respect to the pedals of the bicycle.

SUMMARY

For the sake of rider's comfort and cycling performance while riding the bicycle, the cleats need to be properly adjusted with respect to the soles of the bicycle shoes. In particular, it has been discovered that, for efficiently transferring cycling power to the pedals, the cleats need to be adequately positioned with respect to the rider's feet.

One object of the present disclosure is to provide a bicycle cleat positioning kit with which a cleat can be properly adjusted with respect to a rider's foot.

In accordance with one aspect of the present disclosure, a bicycle cleat positioning kit includes a reference indicating instrument and a cleat adjusting instrument. The reference indicating instrument includes a shoe reference indicator with respect to a bicycle shoe. The cleat adjusting instrument includes a cleat adjusting indicator indicative of an adjustment amount of a cleat with respect to the shoe reference indicator of the reference indicating instrument.

These and other objects, features, aspects and advantages will become apparent to those skilled in the art from the following detailed description, which, taken in conjunction with the annexed drawings, discloses selected embodiments.

BRIEF DESCRIPTION OF THE DRAWINGS

Referring now to the attached drawings which form a part of this original disclosure:

FIG. 15 is an enlarged view of a left parameter table on the foot locating instrument illustrated in FIG. 2, illustrating parameter values measured by the foot measuring instrument recorded on the left parameter table;

DETAILED DESCRIPTION OF EMBODIMENTS

Selected embodiments will now be explained with reference to the drawings. It will be apparent to those skilled in the art from this disclosure that the following descriptions of the embodiments are provided for illustration only and not for the purpose of limiting the invention as defined by the appended claims and their equivalents.

Figure 1:
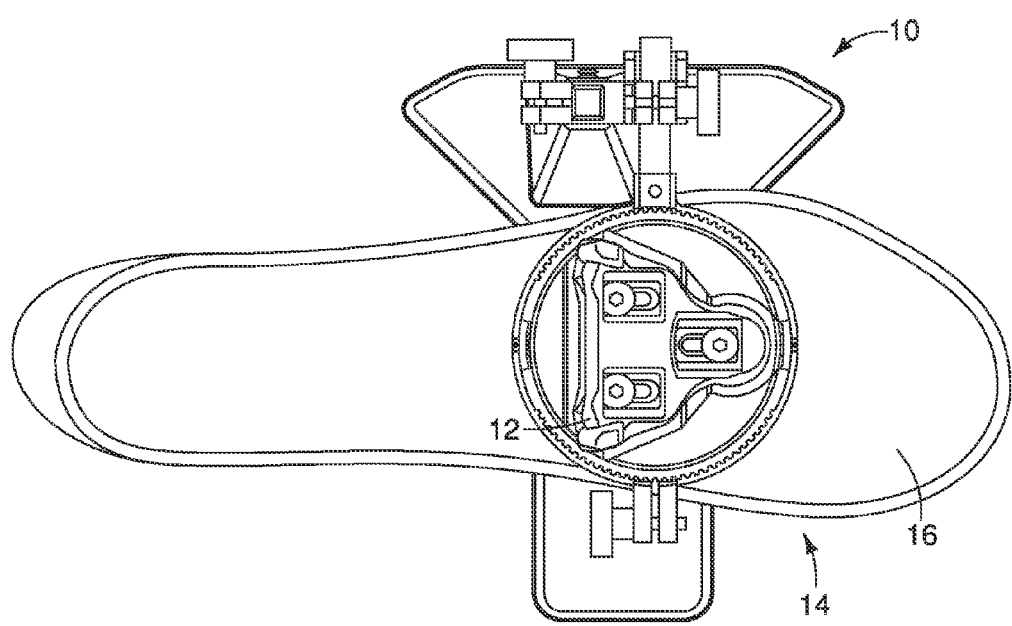
FIG. 1 is a top plan view of a cleat setting device for adjusting a cleat with respect to a shoe sole of a bicycle shoe with the cleat setting device utilized with a bicycle cleat positioning kit in accordance with a first embodiment.
Figure 2:
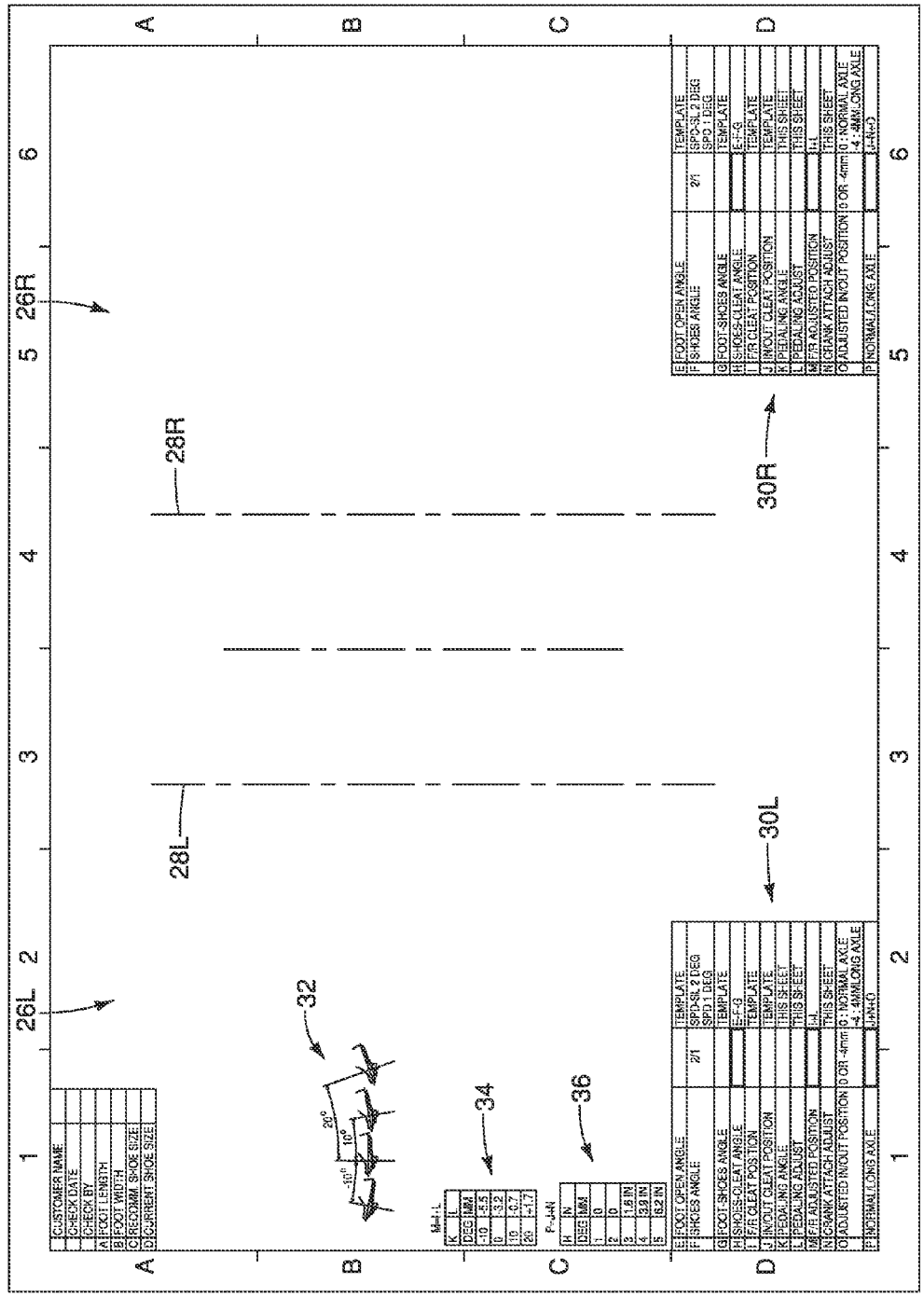
FIG. 2 is a top plan view of a foot locating instrument of the bicycle cleat positioning kit.
Figure 3:
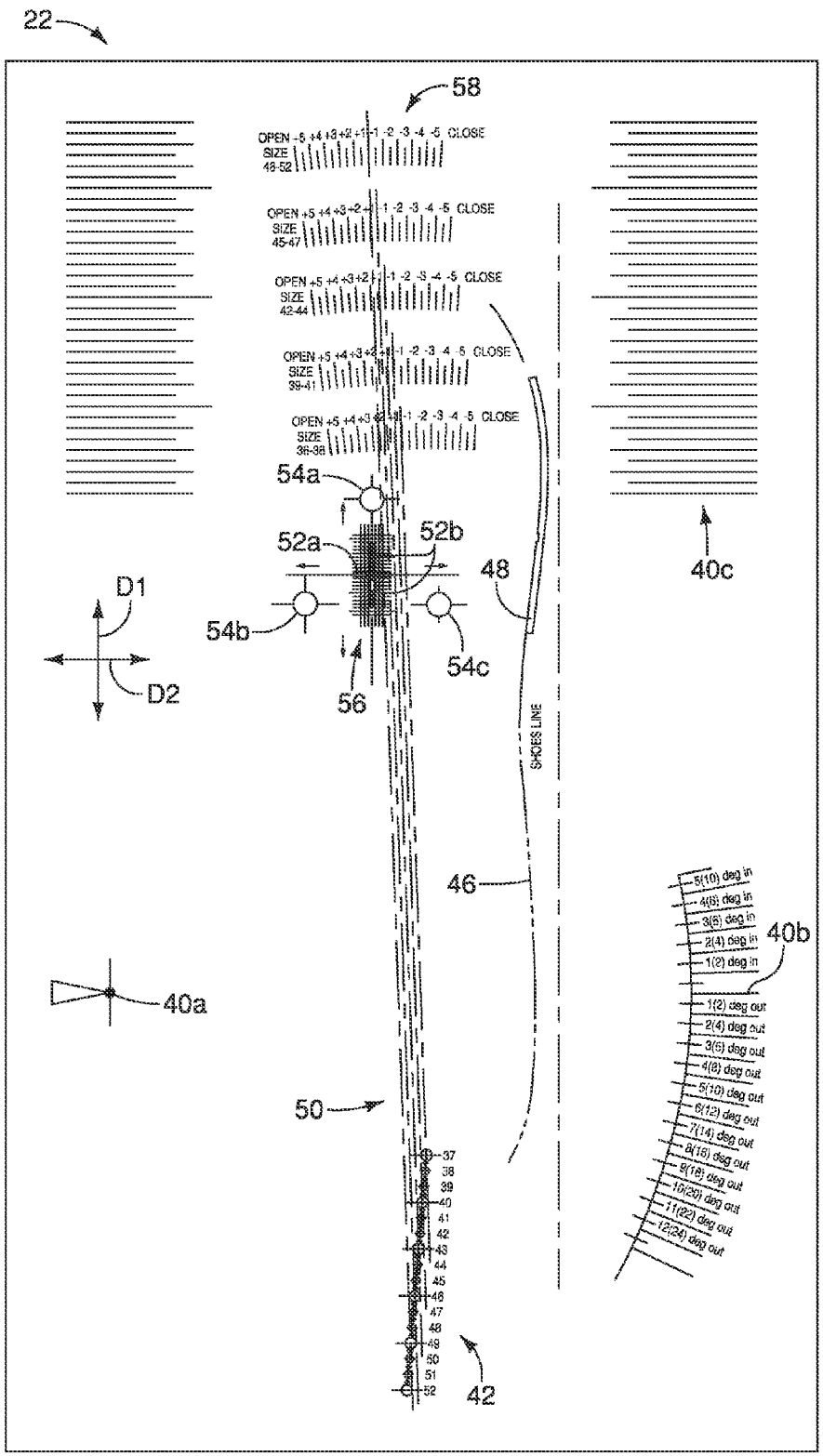
FIG. 3 is a top plan view of a foot measuring instrument of the bicycle cleat positioning kit.

As illustrated in FIG. 1, a cleat setting device 10 is utilized for adjusting a cleat 12 with respect to a bicycle shoe 14 with a bicycle cleat positioning kit in accordance with a first embodiment. The cleat setting device 10 adjusts lengthwise and widthwise locations of the cleat 12 and an orientation of the cleat 12 on a shoe sole 16 of the bicycle shoe 14. The cleat setting device 10 adjusts the cleat 12 with respect to the bicycle shoe 14 based on a plurality of parameter values obtained by the bicycle cleat positioning kit. As illustrated in FIGS. 2 and 3, the bicycle cleat positioning kit basically includes a foot locating instrument 20 and a foot measuring instrument 22. The foot locating instrument 20 and the foot measuring instrument 22 provide the parameter values for the cleat setting device 10 through a bicycle cleat positioning method in accordance with the first embodiment. This bicycle cleat positioning method in accordance with the first embodiment will be described in detail through reference to FIGS. 7 to 18 below.

Figure 4:
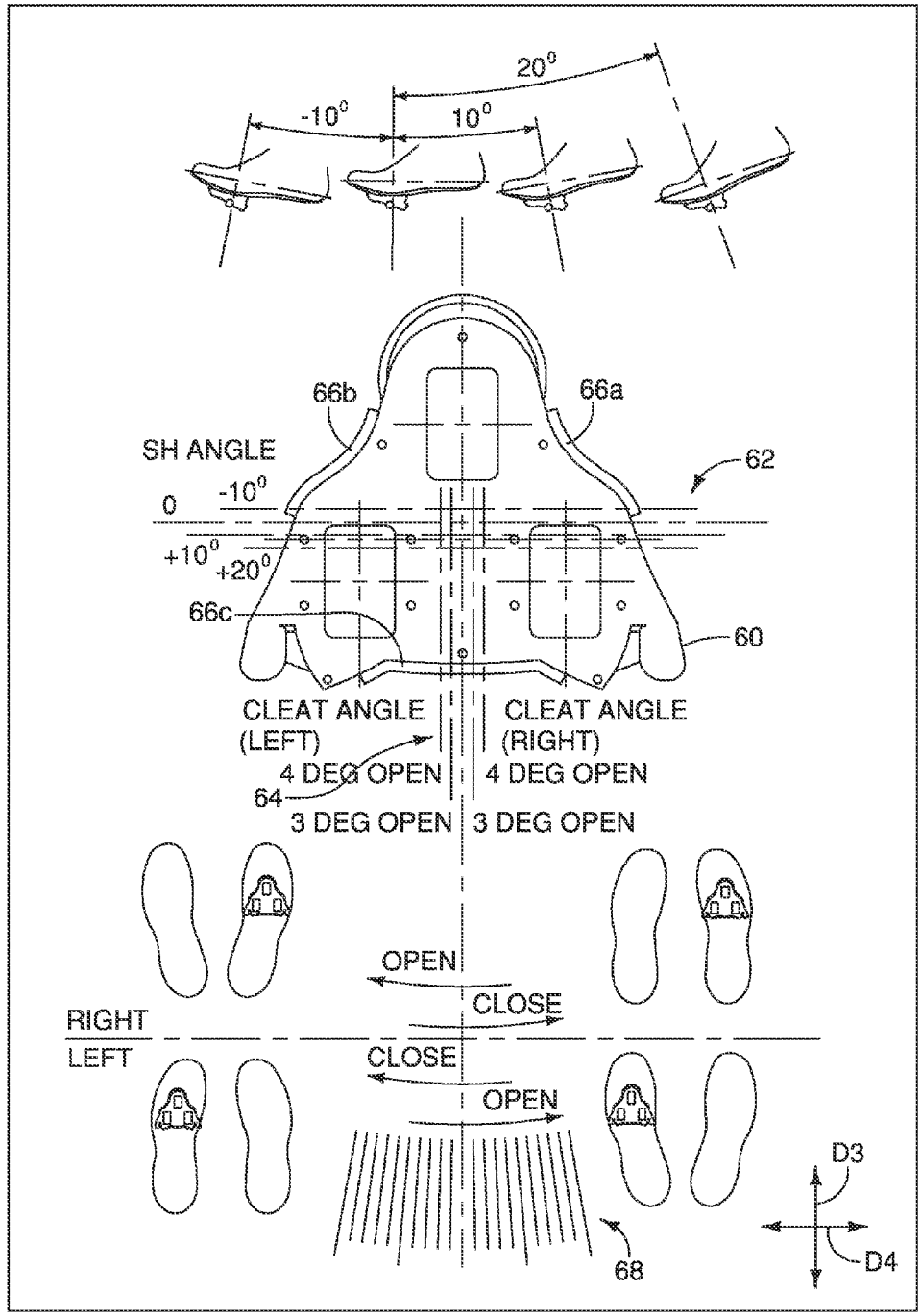
FIG. 4 is a top plan view of a cleat adjusting instrument of the bicycle cleat positioning kit.

Additionally or optionally, as illustrated in FIG. 4, the bicycle cleat positioning kit includes a cleat adjusting instrument 24. The cleat adjusting instrument 24 is utilized for adjusting the cleat 12 with respect to the shoe sole 16 of the bicycle shoe 14 without utilizing the cleat setting device 10. The cleat adjusting instrument 24 determines the lengthwise and widthwise locations of the cleat 12 and the orientation of the cleat 12 on the shoe sole 16 of the bicycle shoe 14 based on the parameter values obtained by the foot locating instrument 20 and the foot measuring instrument 22 through a bicycle cleat positioning method in accordance with a second embodiment. This bicycle cleat positioning method in accordance with the second embodiment will be described in detail through reference to FIGS. 7 to 15 and 19 to 26 below.

Figure 5:
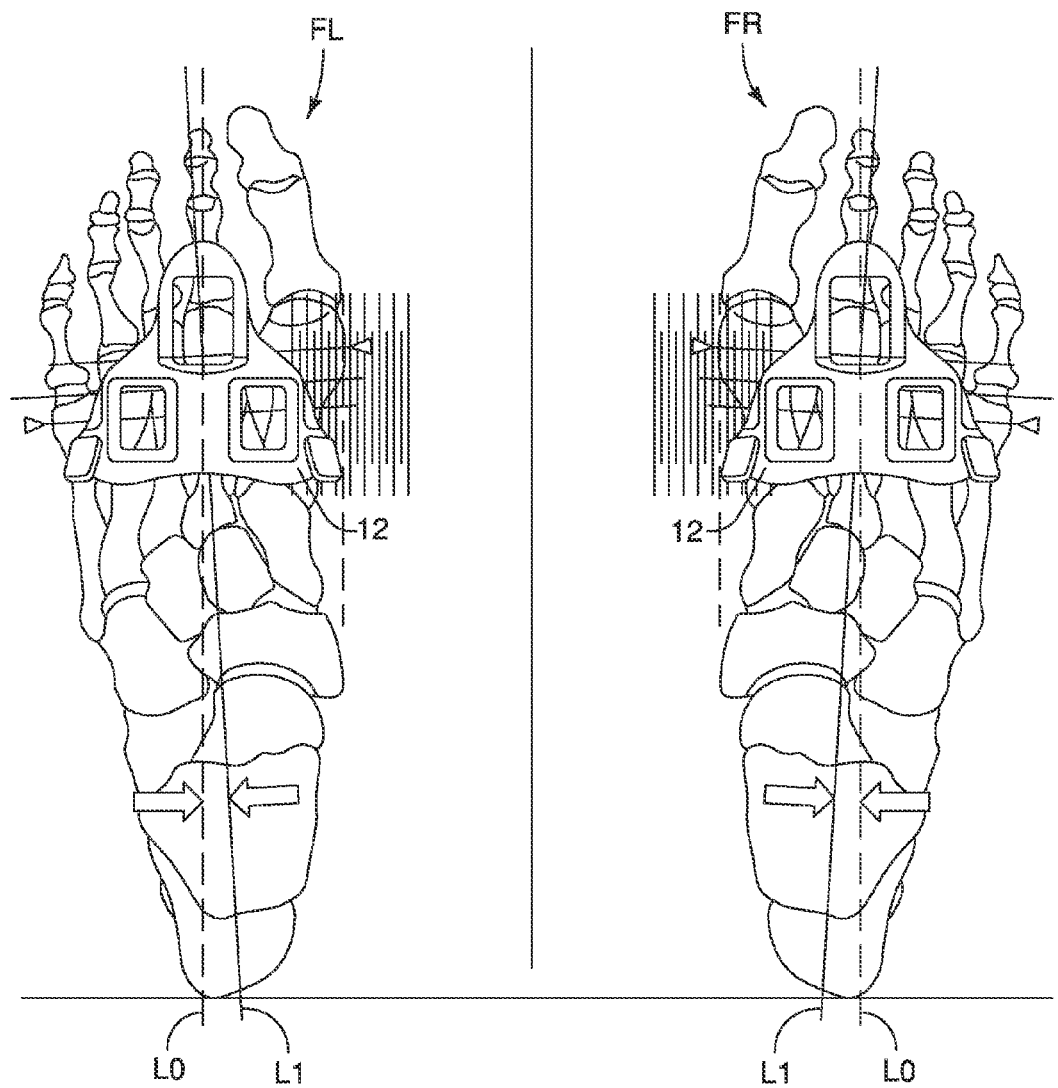
FIG. 5 is a schematic view of a skeletal structure of person's feet illustrating a relationship between the person's feet and the cleats.
Figure 6:
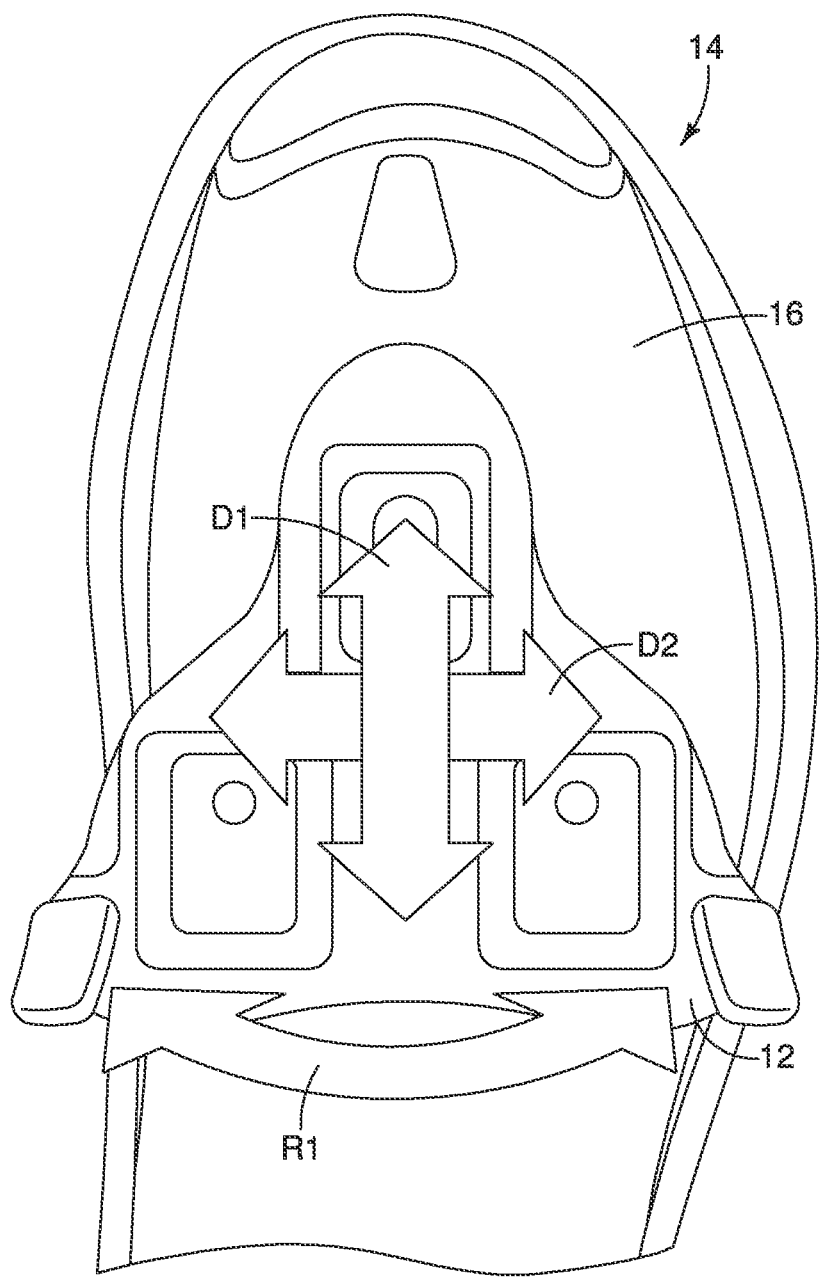
FIG. 6 is a partial bottom plan view of the bicycle shoe with the cleat, illustrating an adjustment of the cleat with respect to the bicycle shoe.

As illustrated in FIGS. 5 and 6, with the bicycle cleat positioning kit and the bicycle cleat positioning method in accordance with the first and second embodiments, the cleats 12 are aligned to the centers of left and right feet FL and FR, respectively, by adjusting the cleats 12 with respect to the shoe soles 16 of the bicycle shoes 14 in lengthwise and widthwise directions D1 and D2. Thus, pedaling power from the person's feet FL and FR can be effectively transferred to the pedal through the bicycle shoes 14 with the cleats 12. Furthermore, the cleats 12 are adjusted in a rotational direction R1 such that center axes L1 of the person's feet FL and FR are oriented to form proper foot opening angles with respect to reference axes L0 of the bicycle. Thus, the cleats 12 can lock the person's feet FL and FR in comfortable postures while riding the bicycle.

Referring now to FIGS. 2 to 4, the bicycle cleat positioning kit will be further described in detail. As illustrated in FIG. 2, the foot locating instrument 20 basically includes a printed sheet member with a foot support surface. The foot support surface of the foot locating instrument 20 basically has left and right foot support portions 26L and 26R. The foot support surface of the foot locating instrument 20 also has left and right crank arm reference indicators 28L and 28R. Furthermore, the foot locating instrument 20 includes left and right parameter tables 30L and 30R, a graphic diagram 32 indicative of pedaling angles, and first and second parameter charts 34 and 36. The left and right foot support portions 26L and 26R, the left and right crank arm reference indicators 28L and 28R, the left and right parameter tables 30L and 30R, the graphic diagram 32, and the first and second parameter charts 34 and 36 are disposed on or printed on the sheet member of the foot locating instrument 20.

The left and right foot support portions 26L and 26R are the areas on which a person (e.g., wearer of the bicycle shoes 14 or rider of the bicycle) places his or her feet FL and FR (see FIG. 5), respectively, while tracing foot outlines L10 (see FIG. 8) of the person's feet FL and FR on the foot support surface of the foot locating instrument 20. The left and right crank arm reference indicators 28L and 28R include parallel lines extending in a direction representing a longitudinal direction (e.g., front to rear direction) of the bicycle. The left and right crank arm reference indicators 28L and 28R are spaced apart from each other by a distance corresponding to a widthwise dimension between crank rotation surfaces of crank arms of the bicycle. The left and right foot support portions 26L and 26R are located outside of a center area between the left and right crank arm reference indicators 28L and 28R with respect to the left and right crank arm reference indicators 28L and 28R, respectively.

The left and right parameter tables 30L and 30R includes a plurality of parameter items. Each of the parameter items includes a parameter names, a parameter value and a remark. The parameter names of the parameter items include "FOOT OPEN ANGLE," "SHOES ANGLE," "FOOT-SHOES ANGLE," "SHOES-CLEAT ANGLE," "F/R CLEAT POSITION," "IN/OUT CLEAT POSITION," "PEDALING ANGLE," "PEDALING ADJUST," "F/R ADJUSTED POSITION," "CRANK ATTACH ADJUST," "ADJUSTED IN/OUT POSITION" and "NOMAL/LONG AXLE." The parameter values are recorded on the left and right parameter tables 30L and 30R after the parameter values are measured by the foot measuring instrument 22 or calculated based on indication of the remarks. The remarks indicate how the parameter values are obtained. Specifically, the remarks indicate that the parameter values are obtained from either a "TEMPLATE," which indicates the foot measuring instrument 22, or a "THIS SHEET," which indicates the foot locating instrument 20. The remarks further indicate alternatives from which the parameter values are chosen, respectively, and formulas by which the parameter values are calculated. The graphic diagram 32 indicates the pedaling angles (e.g., "PEDALING ANGLE") corresponding to different foot postures while pedaling, respectively. The first parameter chart 34 provides adjustment values (e.g., "PEDALING ADJUST") related to the pedaling angles. The second parameter chart 36 provides adjustment values (e.g., "CRANK ATTACH ADJUST") related to different parameter values of "SHOES-CLEAT ANGLE."

As illustrated in FIG. 3, the foot measuring instrument 22 basically includes an alignment point 40a, a foot opening angle scale 40b and a plurality of alignment lines 40c. The foot measuring instrument 22 also includes a plurality of alignment points 42, a shoe reference outline 46 with an alignment section 48. The foot measuring instrument 22 also includes a plurality of shoe reference lines 50. Furthermore, the foot measuring instrument 22 includes a plurality of reference slits 52a and 52b, and a plurality of reference apertures 54a, 54b and 54c. Moreover, the foot measuring instrument 22 includes a positional displacement indicator 56 and an angular displacement indicator 58. The foot measuring instrument 22 includes a transparent sheet member. The alignment point 40a, the foot opening angle scale 40b, the alignment lines 40c, the heel alignment points 42, the shoe reference outline 46, the shoe reference lines 50, the positional displacement indicator 56 and the angular displacement indicator 58 are disposed on or printed on a surface of the transparent sheet member of the foot measuring instrument 22. The reference slits 52a and 52b and the reference apertures 54a, 54b and 54c are formed through the transparent sheet member of the foot measuring instrument 22. The transparent sheet member is made of plastic or other resin material. The foot measuring instrument 22 can alternatively be made of a translucent sheet member. Further, the number of the reference apertures can vary depending of a type of the bicycle shoe 14.

The alignment point 40a, the foot opening angle scale 40b and the alignment lines 40c form an angular displacement indicator for measuring an angular displacement between center lines L11 (see FIG. 8) of the foot outlines L10 traced on the foot locating instrument 20. Specifically, the alignment point 40a, the foot opening angle scale 40b and the alignment lines 40c are arranged with respect to each other such that the foot opening angle scale 40b indicates an angular displacement between the center lines L11 when the alignment point 40a is arranged on one center line L11 and the alignment lines 40c are arranged parallel to the other center line L11. The heel alignment points 42 and the shoe reference outline 46 form a foot reference indicator indicative of a foot reference location with respect to the foot measuring instrument 22. The heel alignment points 42 are provided corresponding to different foot sizes, respectively. Specifically, the heel alignment points 42 represent different heel center positions of feet with different foot sizes, respectively. The shoe reference lines 50 form a shoe reference indicator indicative of a bicycle shoe orientation with respect to the shoe reference outline 46. In particular, the shoe reference lines 50 are provided corresponding to different foot sizes, respectively, and pass through the corresponding heel alignment points 42, respectively. The shoe reference lines 50 represent reference orientations of the bicycle shoes with different foot sizes. The reference slits 52a and 52b, and the reference apertures 54a, 54b and 54c form a cleat attachment indicator indicative of a cleat attachment location relative to the shoe reference outline 46 and the heel alignment points 42. The cleat attachment location indicates a reference location for setting the cleat 12 with respect to the bicycle shoe 14 with the cleat setting device 10. In particular, the reference slits 52a and 52b represent a reference point P15 (e.g., center point) (see FIG. 13) for adjusting the cleat 12 with respect to the bicycle shoe 14. Furthermore, the reference apertures 54a, 54b and 54c represent positions of cleat attachment holes for attaching the cleat 12 to the bicycle shoe 14. The positional displacement indicator 56 is arranged to measure a positional displacement of a center point P10 (see FIG. 8) of each of the foot outlines L10 on the foot locating instrument 20 with respect to the reference point P represented by the reference slits 52a and 52b. The angular displacement indicator 58 includes a plurality of angular scales. Each of the angular scales of the angular displacement indicator 58 is arranged to measure an angular displacement of the center line L11 of each of the foot outlines L10 on the foot locating instrument 20 with respect to a corresponding one of the shoe reference lines 50. Specifically, the angular scales are provided corresponding to different foot size intervals and corresponding to the shoe reference lines 50 such that each of the angular scales measures an angle between the center line L11 of each of the foot outlines L10 and the corresponding one of the shoe reference lines 50 about the corresponding one of the heal alignment points 42.

The foot measuring instrument 22 illustrated in FIG. 3 is basically utilized for the left foot FL. However, the foot measuring instrument 22 can also be utilized for the right foot FR by turning over the foot measuring instrument 22. Since the foot measuring instrument 22 is transparent, the alignment point 40a, the foot opening angle scale 40b, the alignment lines 40c, the heel alignment points 42, the shoe reference outline 46, the shoe reference lines 50, the positional displacement indicator 56 and the angular displacement indicator 58 are visible from both sides of the foot measuring instrument 22. On the other hand, the bicycle cleat positioning kit can also include an additional foot measuring instrument utilized for the right foot FR. In this case, this additional foot measuring instrument has a mirror symmetric arrangement of the foot measuring instrument 22, except for texts on the foot measuring instrument 22.

As illustrated in FIG. 4, the cleat adjusting instrument 24 basically includes a cleat reference indicator 60, a plurality of lengthwise position alignment indicators 62 (e.g., first indicators), a plurality of widthwise position alignment indicators 64 (e.g., second indicators), a plurality of positioning slits 66a, 66b and 66c (e.g., apertures), and a cleat orientation alignment indicator 68. The cleat adjusting instrument 24 includes a transparent sheet member. The cleat reference indicator 60, the lengthwise position alignment indicators 62, the widthwise position alignment indicators 64 and the cleat orientation alignment indicator 68 are disposed on or printed on a surface of the transparent sheet member of the cleat adjusting instrument 24. The positioning slits 66a, 66b and 66c are formed through the transparent sheet member of the cleat adjusting instrument 24. The transparent sheet member is made of plastic or other resin material. The cleat adjusting instrument 24 can alternatively include a translucent sheet member. The cleat adjusting instrument 24 illustrated in FIG. 4 is basically utilized for the left and right feet FL and FR.

The cleat reference indicator 60 indicates a cleat outline. The lengthwise position alignment indicators 62 and the widthwise position alignment indicator 64 form a cleat position alignment indicator indicative of different positions of the center point P10 (see FIG. 8) of each of the foot outlines L10 on the foot locating instrument 20 with respect to the cleat reference indicator 60. The lengthwise position alignment indicators 62 represent lengthwise positions (e.g., first foot center locations) of the center point P10 of each of the foot outlines L10 with respect to the cleat reference indicator 60 in a lengthwise direction D3 (e.g., first direction) of the cleat reference indicator 60, respectively. The lengthwise position alignment indicators 62 are provided corresponding to different pedaling angles. The widthwise position alignment indicators 64 represent widthwise positions (e.g., second foot center locations) of the center point P10 of each of the foot outlines L10 with respect to the cleat reference indicator 60 in a widthwise direction D4 (e.g., second direction) of the cleat reference indicator 60, respectively. The widthwise direction D4 is perpendicular to the lengthwise direction D3. The widthwise position alignment indicators 64 are provided corresponding to different cleat angles (e.g., bicycle cleat orientations) with respect to the bicycle shoe 14. The lengthwise and widthwise directions D3 and D4 are perpendicular to each other. The positioning slits 66a, 66b and 66c extend along an outer peripheral of the cleat reference indicator 60. The cleat orientation alignment indicator 68 indicates an orientation of the cleat reference indicator 60 with respect to each of the center lines L11 of the foot outlines L10.

Referring now to FIGS. 7 to 18, the bicycle cleat positioning method in accordance with the first embodiment will now be described in detail. The foot locating instrument 20 (see FIG. 2) and the foot measuring instrument 22 (see FIG. 3) provide the parameter values for the cleat setting device 10 (see FIG. 1) through this bicycle cleat positioning method.

Figure 7:
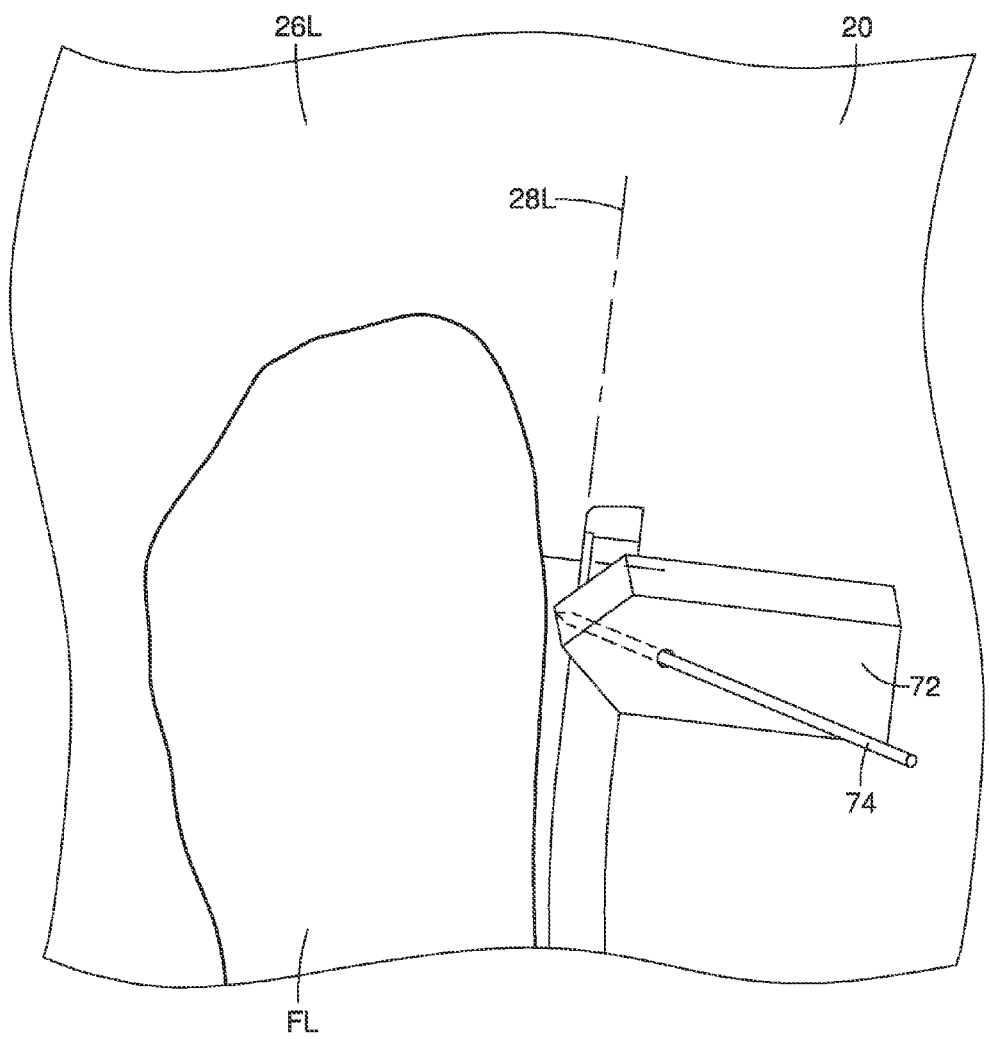
FIG. 7 is an enlarged view of the foot locating instrument illustrated in FIG. 2, illustrating a tracing of an outline of the person's foot on the foot locating instrument.
Figure 8:
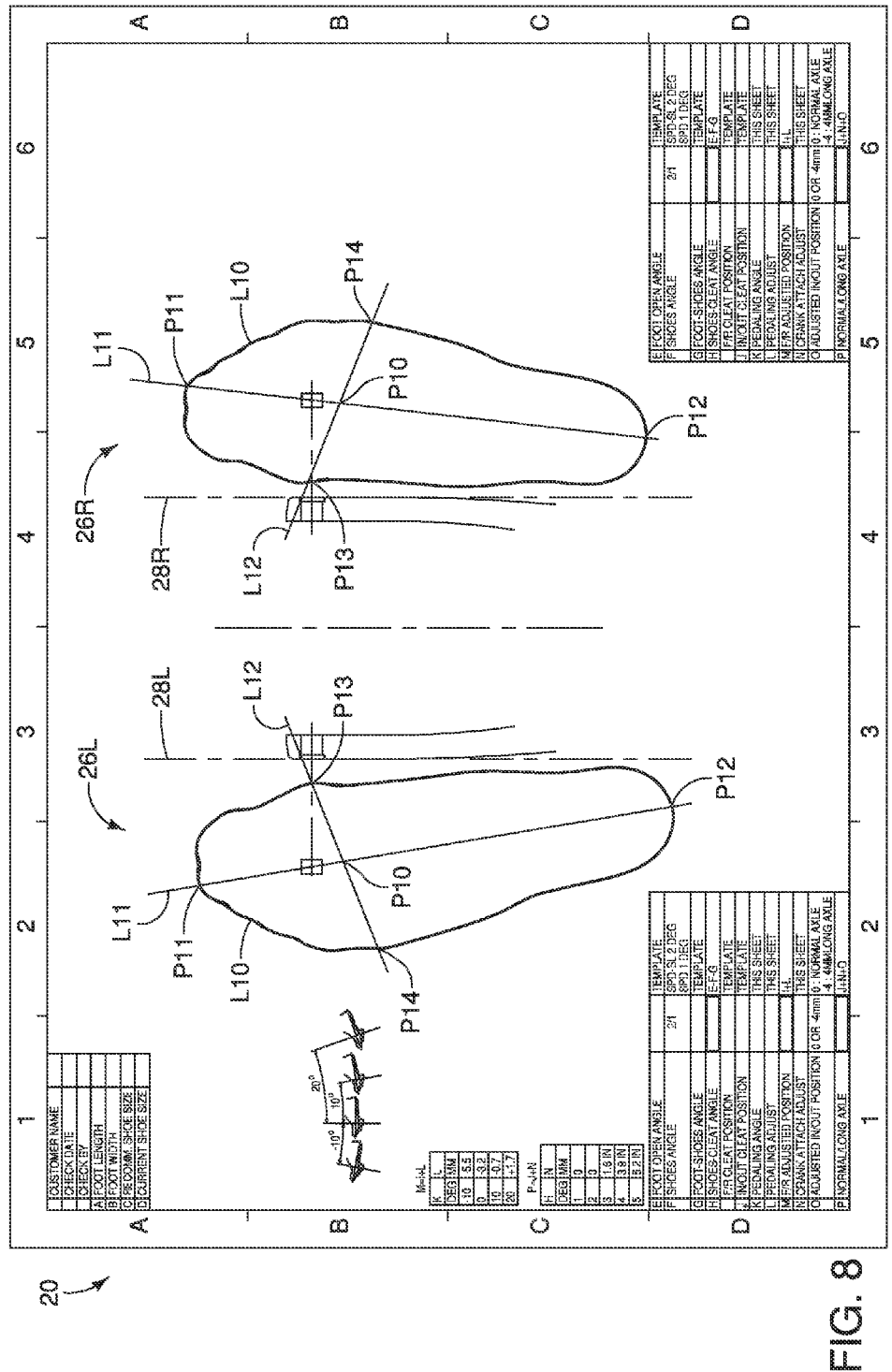
FIG. 8 is a top plan view of the foot locating instrument illustrated in FIG. 2, illustrating foot outlines of the person's feet traced on the foot locating instrument.

As illustrated in FIGS. 7 and 8, the bicycle cleat positioning method basically includes manually tracing outlines of the person's feet FL and FR on the foot locating instrument 20. In particular, as illustrated in FIG. 7, the person places his or her feet FL and FR on the foot locating instrument 20 at the left and right foot support portions 26L and 26R outside the left and right crank arm reference indicators 28L and 28R, respectively. Specifically, the person places his or her feet FL and FR on the foot locating instrument 20 such that the feet FL and FR is arranged in his or her neutral or comfortable position for riding the bicycle. For better understanding of this procedure, FIG. 7 only illustrates that the left foot FL is placed on the foot locating instrument 20 at the left foot support portion 26L outside the left crank arm reference indicator 28L. The outlines of the person's feet FL and FR are traced with a tracing device 72 having a writing instrument 74, such as a ballpoint pen and the like. In particular, the tracing device 72 is slid around the person's feet FL and FR on the foot locating instrument 20 along the outlines of the person's feet FL and FR, by which the writing instrument 74 marks the left and right foot support portion 26L and 26R with the foot outlines L10, as illustrated in FIG. 8.

Furthermore, as illustrated in FIG. 8, the bicycle cleat positioning method includes marking the foot locating instrument 20 with the center points P10 of the foot outlines L10 of the person's feet FL and FR and the center lines L11 (e.g., center axes) of the foot outlines L10 of the person's feet FL and FR. In particular, after tracing the foot outlines L10 on the foot locating instrument 20, a toe center position P11, a heel center position P12, a thenar apex position P13 and a antithenar apex position P14 are determined on each of the foot outlines L10. The toe center position P11 is determined as an apex position of a convex segment of each of the foot outlines L10 that represents the second finger of each of the person's feet FL and FR. The heel center position P12 is determined as an apex position of a convex segment of each of the foot outlines L10 that represents the heel of each of the person's feet FL and FR. The thenar apex position P13 is determined as an apex position of a convex segment of each of the foot outlines L10 that represents a ball of the thumb of each of the person's feet FL and FR. The antithenar apex position P14 is determined as an apex position of a convex segment of each of the foot outlines L10 that represents a ball of the fifth finger of each of the person's feet FL and FR. Then, the center lines L11 of the foot outlines L10 are drawn on the foot locating instrument 20 such that the center lines L11 pass through the toe center positions P11 and the heel center positions P12, respectively. Furthermore, transverse lines L12 of the foot outlines L10 are drawn on the foot locating instrument 20 such that the transverse lines L12 pass through the thenar apex positions P13 and the antithenar apex positions P14, respectively. Moreover, intersections of the center lines L11 and the transverse lines L12 inside the foot outlines are determined as the center points P10 of the foot outlines L10. Here, as illustrated FIGS. 7 and 8, the foot locating instrument 20 additionally or optionally includes graphic indicators indicative of crank arms and pedal axes as a reference for easy positioning the person's feet FL and FR on the left and right foot support portions 26L and 26R. However, the foot locating instrument 20 does not necessarily include the graphic indictors as illustrated FIG. 2.

Figure 9:
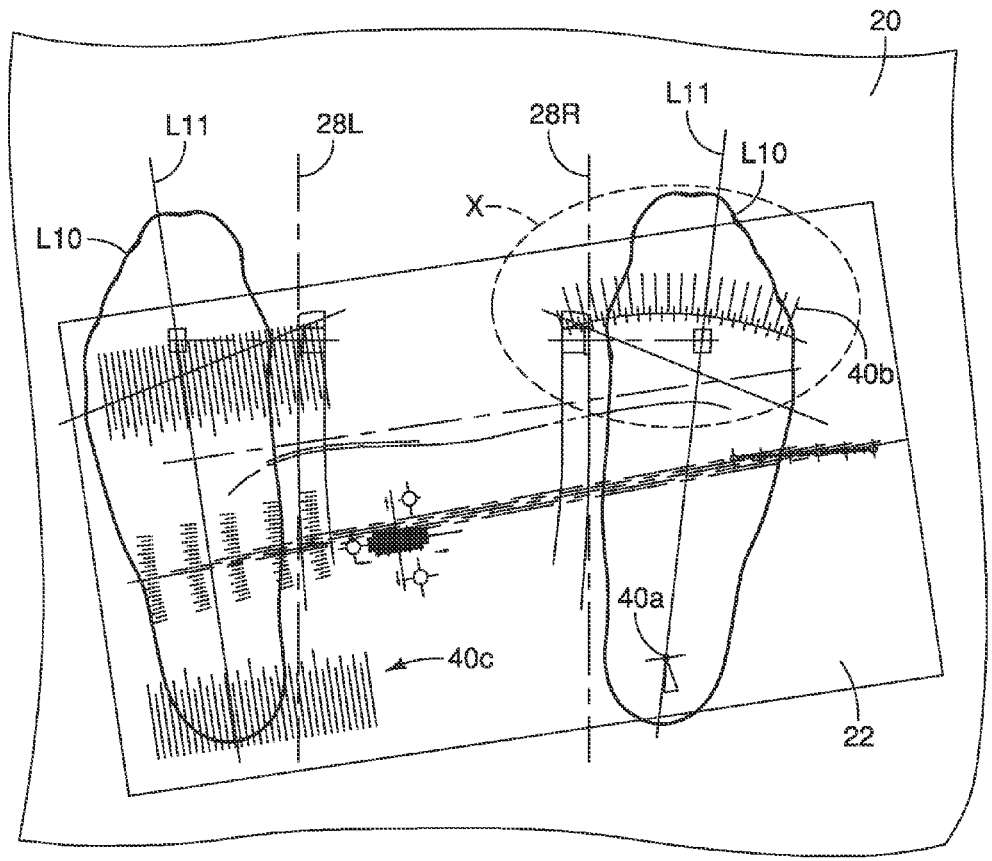
FIG. 9 is a top plan view of the foot locating instrument illustrated in FIG. 2 and the foot measuring instrument illustrated in FIG. 3, illustrating the foot measuring instrument overlaid on the foot locating instrument to measure an angle between center lines of the foot outlines of the person's feet on the foot locating instrument.
Figure 10:
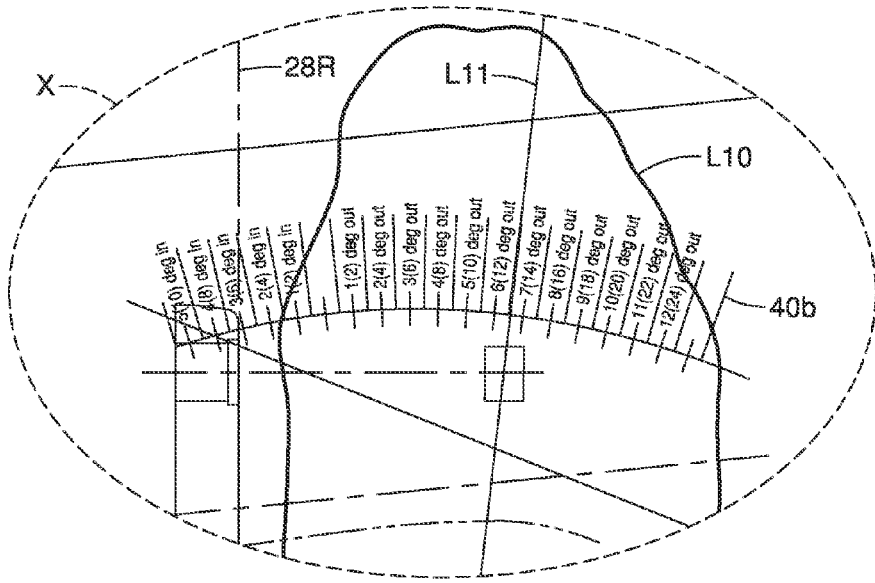
FIG. 10 is an enlarged view of an encircled portion X in FIG. 9, illustrating the angle between the center lines of the foot outlines of the person's feet on the foot locating instrument measured by the foot measuring instrument.

As illustrated in FIGS. 9 and 10, the bicycle cleat positioning method further includes overlying the foot measuring instrument 22 on the foot locating instrument 20, and measuring the foot opening angles (e.g., "FOOT OPEN ANGLE" in FIG. 2) of the center lines L11 of the foot outlines L10 on the foot locating instrument 20 with respect to the left and right crank arm reference indicators 28L and 28R. Specifically, the foot measuring instrument 22 is overlaid on the foot locating instrument 20, and aligned with respect to the foot locating instrument 20 such that the alignment point 40a is arranged on the center line L11 of the foot outline L10 of the person's right foot FR, and such that the alignment lines 40c are arranged parallel to the center line L11 of the person's left foot FL. With this alignment, as illustrated in FIG. 10, the foot opening angle scale 40b indicates the foot opening angles of the center lines L11 of the foot outlines L10 on the foot locating instrument 20 with respect to the left and right crank arm reference indicators 28L and 28R as a half of an angle formed between the center lines L11. For example, FIG. 10 illustrates that the foot opening angle scale 40b indicates "6(12) deg out," which means that the angle between the center lines L11 is "12 degrees", the foot opening angles of the center lines L11 with respect to the left and right crank arm reference indicators 28L and 28R are "6 degrees," and that the foot outlines L10 of the person's feet FL and FR are arranged in an open stance. Then, the foot opening angles of the person's feet FL and FR are written down in the left and right parameter tables 30L and 30R as parameter values of the "FOOT OPEN ANGLE." Here, the foot opening angles are obtained as a half of the angle between the center lines L11. However, the foot opening angles can also be obtained by measuring angles between the center lines L11 and the left and right crank arm reference indicators 28L and 28R, respectively. Furthermore, with the foot opening angle scale 40b, a rotational direction that makes the stance more open is defined as a positive direction.

Figure 11:
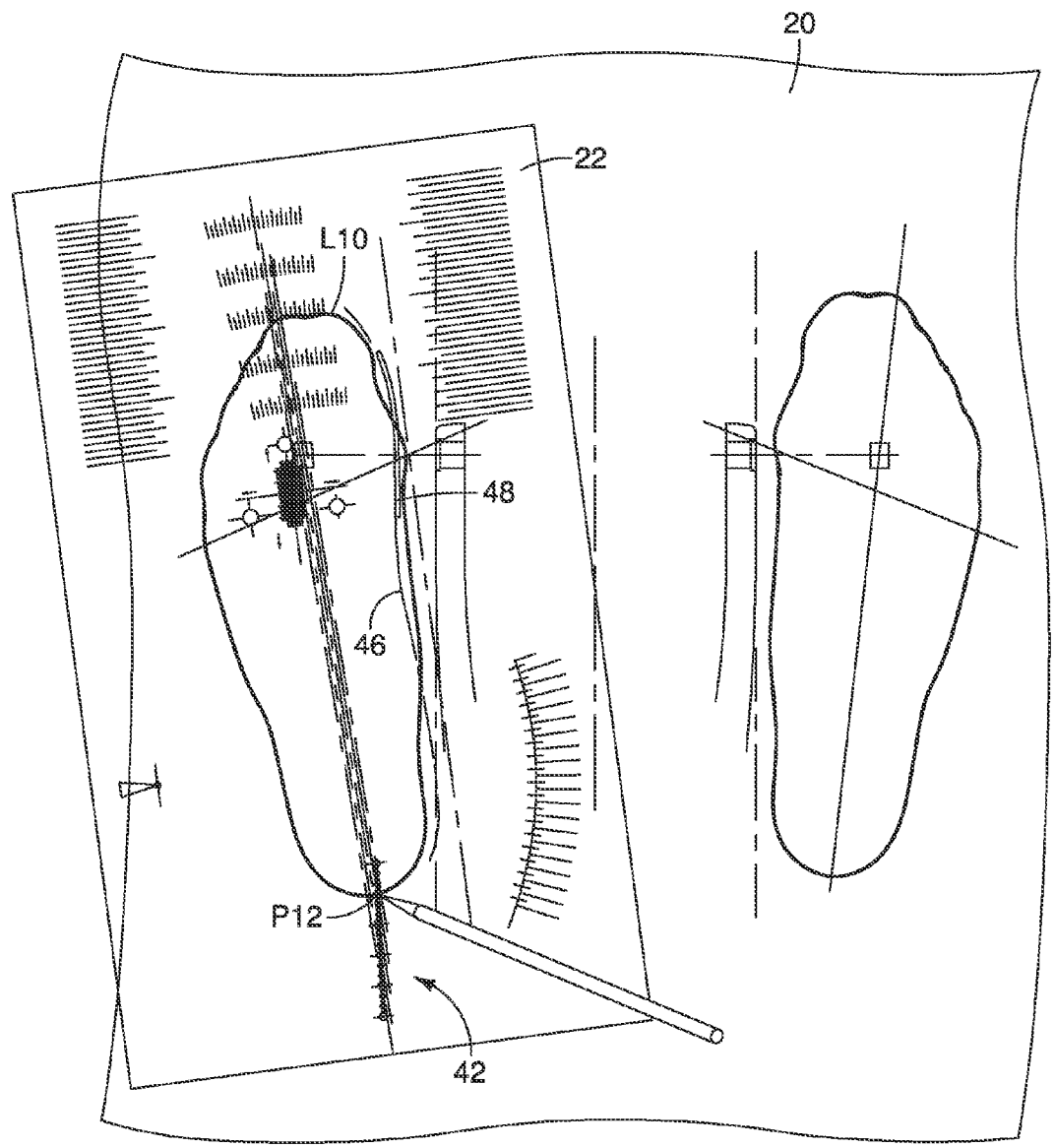
FIG. 11 is a top plan view of the foot locating instrument illustrated in FIG. 2 and the foot measuring instrument illustrated in FIG. 3, illustrating the foot measuring instrument overlaid on the foot locating instrument such that a heel center position of the foot outline of the person's foot on the foot locating instrument is aligned to a heel alignment point on the foot measuring instrument.
Figure 12:
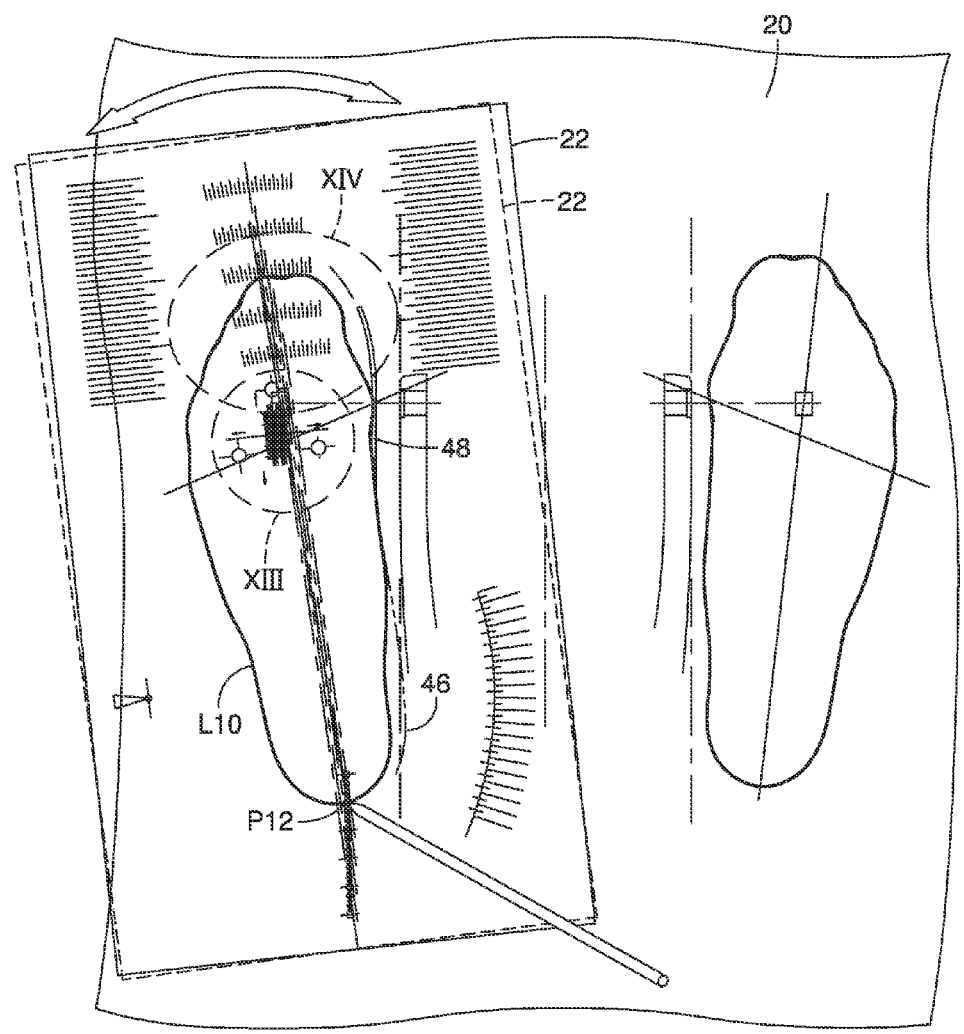
FIG. 12 is a top plan view of the foot locating instrument illustrated in FIG. 2 and the foot measuring instrument illustrated in FIG. 3, illustrating the foot measuring instrument rotated around the heel alignment point on the foot measuring instrument with respect to the foot locating instrument such that an alignment section of a shoe reference outline on the foot measuring instrument is aligned to a part of the foot outline of the person's foot on the foot locating instrument.

As illustrated in FIGS. 11 and 12, the bicycle cleat positioning method further includes overlying the foot measuring instrument 22 on the foot locating instrument 20, and aligning the foot measuring instrument 22 to the foot outline L10 on the foot locating instrument 20 using the heel alignment points 42 and the shoe reference outline 46 on the foot measuring instrument 22. Specifically, before this procedure, foot sizes of the person's feet FL and FR are measured in a conventional manner. Furthermore, hereinafter, the bicycle cleat positioning method applied to the person's left foot FL is identical to the bicycle cleat positioning method applied to the person's right foot FR. Thus, only the bicycle cleat positioning method applied to the person's left foot FL will be discussed herein for the sake of brevity.

As illustrated in FIG. 11, the foot measuring instrument 22 is aligned with respect to the foot locating instrument 20 such that one of the heel alignment points 42 that corresponds to the measured foot size of the person's left foot FL is aligned to the heel center position P12 of the foot outline L10. Then, the foot measuring instrument 22 is pivotally pined to the foot locating instrument 20 at the one of the heel alignment points 42 with a pinning instrument, such as a pin, a tip of a pen, and the like. Furthermore, the foot measuring instrument 22 is pivoted in a clockwise direction or a counterclockwise direction about the one of the heel alignment points 42 such that the alignment section 48 of the shoe reference outline 46 is located on an inside portion of the foot outline L10 on the foot locating instrument 20, as illustrated in FIG. 12. The alignment section 48 is wider than the shoe reference outline 46, and is about two millimeter wide. Thus, the alignment section 48 is easily aligned to the inside portion of the foot outline L10 such that the alignment section 48 overlaps the inside portion of the foot outline L10. Here, the alignment section 48 of the shoe reference outline 46 represents an inside portion of a foot outline. However, the foot measuring instrument 22 can alternatively include an alignment section of a show reference outline that represents an outside portion of a foot outline. In this case, the foot measuring instrument 22 is pivoted to align the alignment section of the shoe reference outline to the outside portion of the foot outline.

Figure 13:
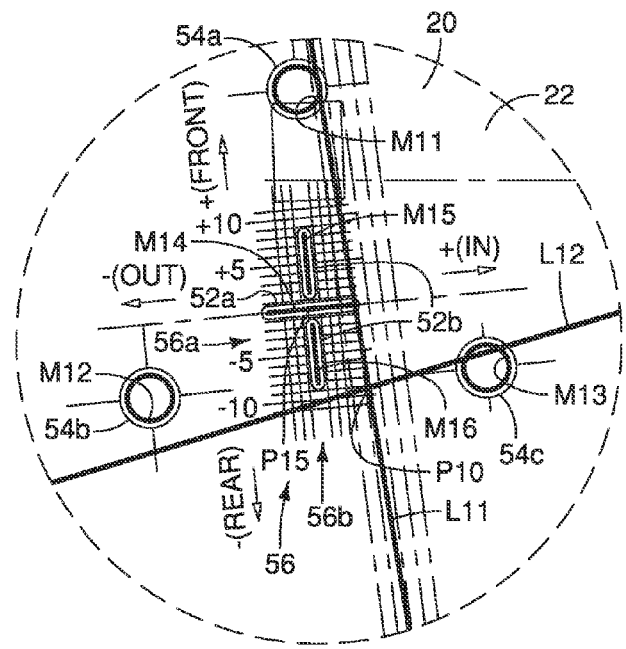
FIG. 13 is an enlarged view of an encircled portion XIII in FIG. 12, illustrating a positional displacement of a center point of the foot outline of the person's foot on the foot locating instrument with respect to a reference point on the foot measuring instrument measured by the foot measuring instrument.

Next, as illustrated in FIG. 13, the bicycle cleat positioning method further includes marking the foot locating instrument 20 with circular marks M11, M12 and M13, and linear marks M14, M15 and M16. The circular marks M11, M12 and M13 are traced on the foot locating instrument 20 through the reference apertures 54a, 54b and 54c on the foot locating instrument 20, respectively. The circular marks M11, M12 and M13 represent positions of the cleat attachment holes (e.g., cleat attachment locations) on the shoe sole 16 of the bicycle shoe 14 with respect to the foot outline L10. The linear marks M14, M15 and M16 are traced on the foot locating instrument 20 through the reference slits 52a and 52b on the foot locating instrument 20, respectively. The linear marks M14, M15 and M16 represent the reference point P15 of the cleat attachment location (e.g., center position of the cleat attachment holes) on the shoe sole 16 of the bicycle shoe 14 with respect to the foot outline L10. In particular, an intersection of an axis extending along the linear mark M14 and an axis extending along the linear marks M15 and M16 indicates the reference point P15 of the cleat attachment location.

Furthermore, as illustrated in FIG. 13, the bicycle cleat positioning method further includes measuring the positional displacement of the center point P10 of the foot outline L10 on the foot locating instrument 20 with respect to the reference point P15 of the cleat attachment location indicated by the linear marks M14, M15 and M16 on the foot measuring instrument 22. The positional displacement of the center point P10 with respect to the reference point P15 of the cleat attachment location is measured by the positional displacement indicator 56. In particular, the positional displacement indicator 56 includes fine lines making up a regular grid with the reference point P15 of the cleat attachment location as the origin of the regular grid. The positional displacement indicator 56 includes a longitudinal position scale 56a (e.g., first measuring scale) and a transverse position scale 56b (e.g., second measuring scale). The longitudinal position scale 56a includes parallel lines extending in the widthwise (or transverse) direction D2 of the foot measuring instrument 22. The longitudinal position scale 56a measures a longitudinal displacement between the center point P10 and the reference point P15 of the cleat attachment location in the lengthwise (or longitudinal) direction D1 of the foot measuring instrument 22. For example, in FIG. 13, the longitudinal position scale 56a indicates that the longitudinal displacement is "−9." Then, the longitudinal displacement value is written down in the left parameter table 30L in FIG. 2 as a parameter value of the "F/R CLEAT POSITION." Furthermore, the transverse position scale 56b includes parallel lines extending in the lengthwise direction D1 of the foot measuring instrument 22. The transverse position scale 56b measures a transverse displacement between the center point P10 and the reference point P15 of the cleat attachment location in the widthwise direction D2 of the foot measuring instrument 22. For example, in FIG. 13, the transverse position scale 56b indicates that the transverse displacement is "6." Then, the transverse displacement value is written down in the left parameter table 30L in FIG. 2 as a parameter value of the "IN/OUT CLEAT POSITION." Here, with the positional displacement indicator 56, a lengthwise direction approaching the toe is defined as a positive lengthwise direction, and a widthwise direction approaching the left crank arm reference indicator 28L is defined as a positive widthwise direction.

Figure 14:
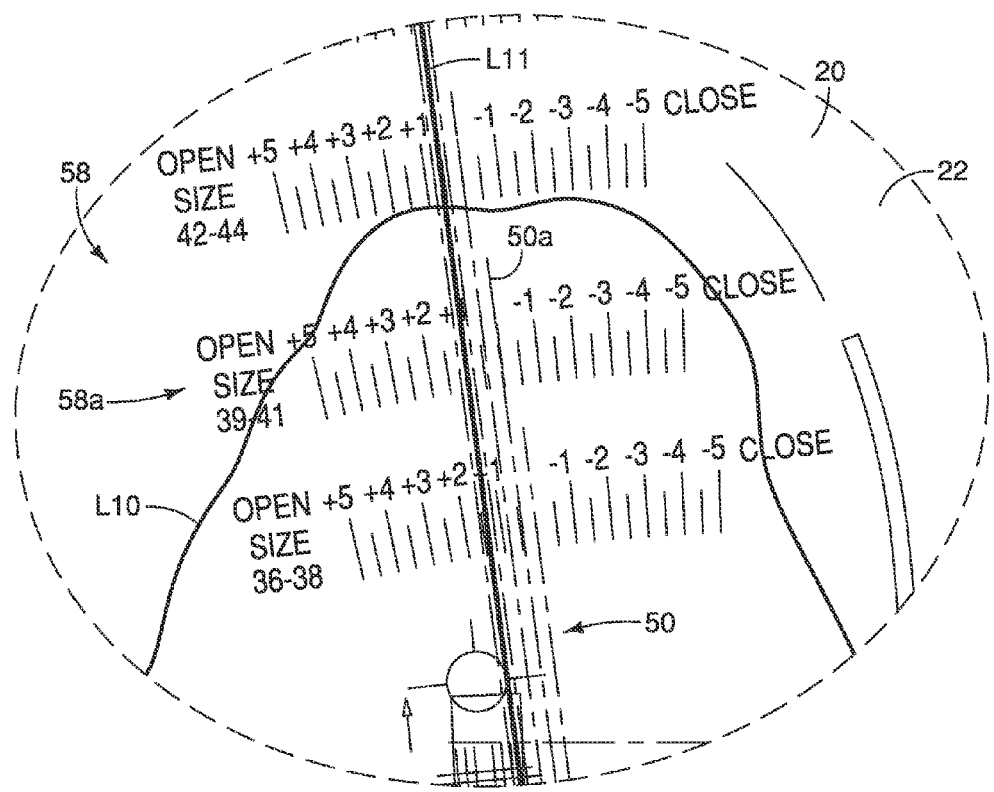
FIG. 14 is an enlarged view of an encircled portion XIV in FIG. 12, illustrating an angular displacement of the center line of the foot outline of the person's foot on the foot locating instrument with respect to a shoe reference line on the foot measuring instrument measured by the foot measuring instrument.

Next, as illustrated in FIG. 14, the bicycle cleat positioning method further includes measuring an angular displacement of the center line L11 of the foot outline L10 on the foot locating instrument 20 with respect to one of the shoe reference lines 50 that corresponds to the measured foot size of the person's foot FL. For example, when the measured foot size is "40," then the angular displacement of the center line L11 of the foot outline L10 with respect to a shoe reference line 50a of the shoe reference lines 50 is measured with an angular scale 58a of the angular displacement indicator 58, as illustrated in FIG. 14. The shoe reference line 50a of the shoe reference lines 50 passes through one of the heel alignment points 42 corresponding to the measured foot size "40." The angular scale 58a of the angular displacement indicator 58 is provided corresponding to a foot size interval "39-41." For example, in FIG. 14, the angular scale 58a indicates that the angular displacement is "+1." Then, the angular displacement value is written down in the left parameter table 30L in FIG. 2 as a parameter value of the "FOOT-SHOES ANGLE." With the angular displacement indicator 58. A rotational direction that makes the stance more open relative to the left crank arm reference indicator 28L is defined as a positive direction.

Figure 16:
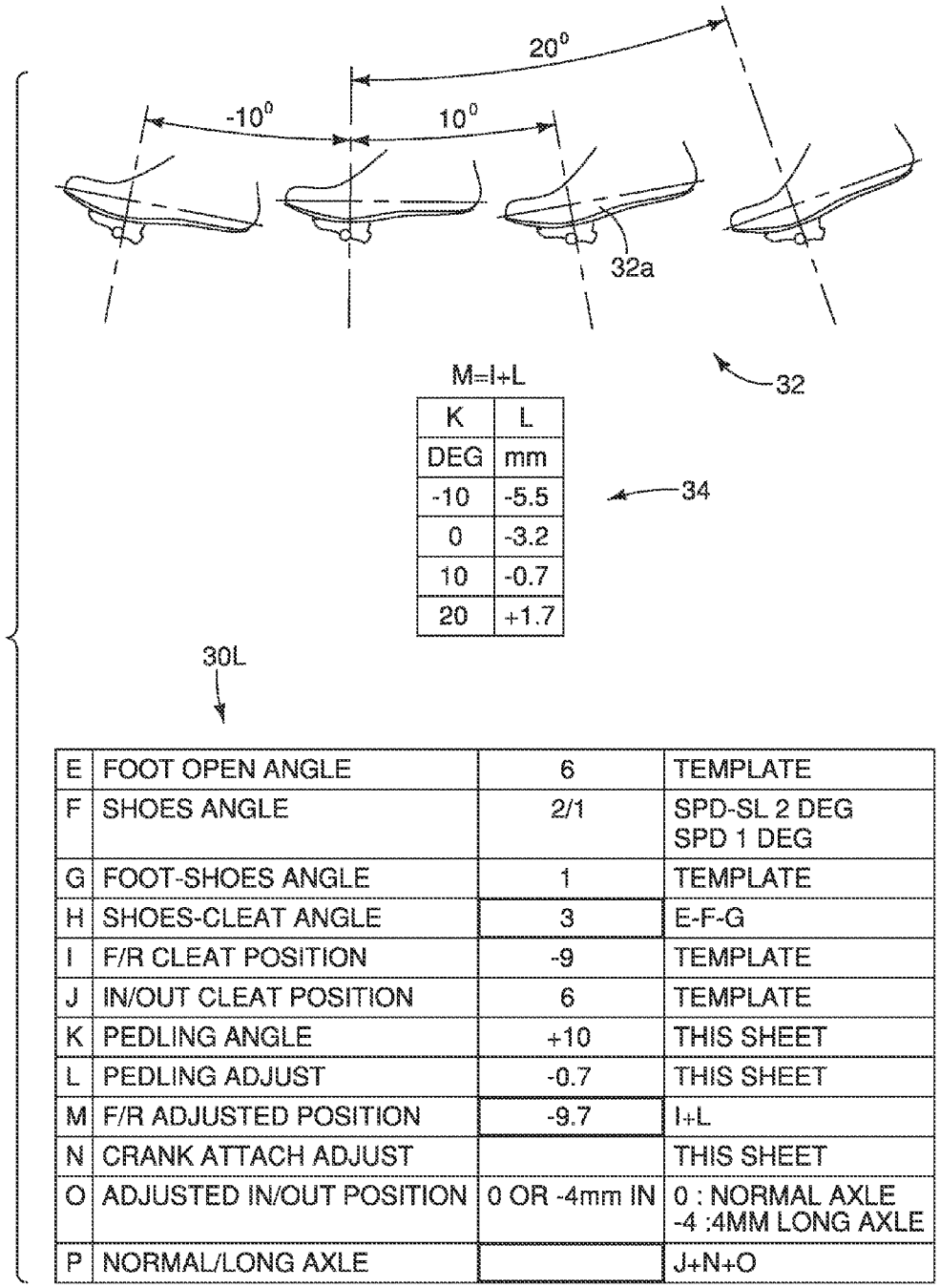
FIG. 16 is enlarged views of a graphic diagram indicative of pedaling angles, a first parameter chart of adjustment values corresponding to the pedaling angles, and the left parameter table on the foot locating instrument illustrated in FIG. 2, illustrating a parameter value calculated based on the first parameter chart recorded on the left parameter table.
Figure 17:
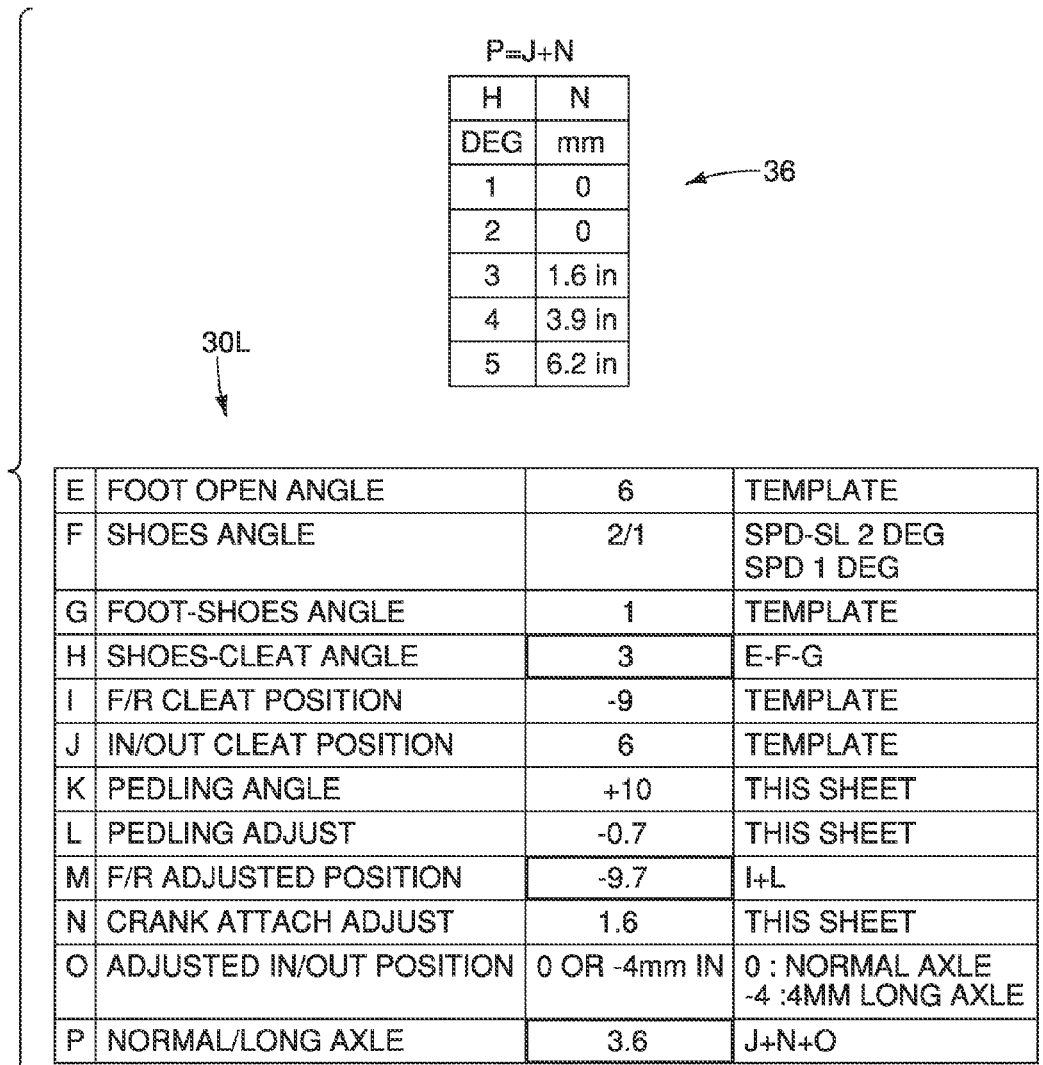
FIG. 17 is enlarged views of a second parameter chart of adjustment values corresponding to shoes-cleat angles, and the left parameter table on the foot locating instrument illustrated in FIG. 2, illustrating a parameter value calculated based on the second parameter chart recorded on the left parameter table.

As illustrated in FIGS. 15 to 17, the bicycle cleat positioning method further includes calculating the parameter values of the "SHOES-CLEAT ANGLE," the "F/R ADJUSTED POSITION," and the "NOMAL/LONG AXLE" for the cleat setting device 10. First, as illustrated in FIG. 15, the parameter value of the "SHOES-CLEAT ANGLE" is calculated based on the parameter values of the "FOOT OPEN ANGLE," the "SHOES ANGLE," and the "FOOT-SHOES ANGLE" by subtracting the parameter values of the "SHOES ANGLE" and the "FOOT-SHOES ANGLE" from the parameter value of the "FOOT OPEN ANGLE." The parameter value of the "FOOT OPEN ANGLE" is measured using the foot opening angle scale 40b as illustrated in FIG. 10, and the parameter value of the "FOOT-SHOES ANGLE" is measured using the angular displacement indicator 58 as illustrated in FIG. 14. Furthermore, the parameter value of the "SHOES ANGLE" is determined by a cleat type of the cleat 12. In particular, if the cleat type of the cleat 12 is "SPD-SL," then the parameter value of the "SHOES ANGLE" is set to "2." On the other hand, if the cleat type of the cleat 12 is "SPD," then the parameter value of the "SHOES ANGLE" is set to "1."

For example, as illustrated in FIG. 15, the parameter value of the "FOOT OPEN ANGLE" is measured as "6." and the parameter value of the "FOOT-SHOES ANGLE" is measured as "1." Furthermore, the parameter value of the "SHOES ANGLE" is set to "2." Thus, the parameter value of the "SHOES-CLEAT ANGLE" is calculated as "3". Then, the parameter value of the "SHOES-CLEAT ANGLE" is written down in the left parameter table 30L as illustrated in FIG. 15.

Next, as illustrated in FIG. 16, the parameter value of the "F/R ADJUSTED POSITION" is calculated based on the parameter values of the "F/R CLEAT POSITION" and the "PEDALING ADJUST" by adding the parameter values of the "F/R CLEAT POSITION" and the "PEDALING ADJUST." The parameter value of the "F/R CLEAT POSITION" is measured using the longitudinal position scale 56a as illustrated in FIG. 13. The parameter value of the "PEDALING ADJUST" is determined by the parameter value of the "PEDALING ANGLE" and the first parameter chart 34 as illustrated in FIG. 16. In particular, the parameter value of the "PEDALING ANGLE" is determined by a foot posture of the person's foot while pedaling as illustrated in the graphic diagram 32. For example, the person or a cleat fitter who adjusts the cleat observes the foot posture of the person's foot while pedaling, and determines the parameter value of the "PEDALING ANGLE" from alternatives ("−10," "0," "10," or "20") illustrated in the graphic diagram 32. The first parameter chart 34 provides the parameter values of the "PEDALING ADJUST" corresponding to the parameter values of the "PEDALING ANGLE." The parameter values of the "PEDALING ADJUST" are predetermined such that the cleat 12 is placed vertically below the center point of the person's foot even if the center point of the person's foot is displaced around the pedaling axle in accordance with the pedaling angles of the person's foot.

For example, as illustrated in FIG. 16, the parameter value of the "F/R CLEAT POSITION" is measured as "−9." Furthermore, the parameter value of the "PEDALING ADJUST" is set to "−0.7" when the foot posture of the person's foot is determined as a posture 32a, and the parameter value of the "PEDALING ANGLE" is determined as "+10." Thus, the parameter value of the "F/R ADJUSTED POSITION" is calculated as "−9.7". Then, the parameter value of the "F/R ADJUSTED POSITION" is written down in the left parameter table 30L as illustrated in FIG. 16.

Furthermore, as illustrated in FIG. 17, the parameter value of the "NOMAL/LONG AXLE" is calculated based on the parameter values of the "IN/OUT CLEAT POSITION," the "CRANK ATTACH ADJUST," and the "ADJUSTED IN/OUT POSITION" by adding the parameter values of the "IN/OUT CLEAT POSITION." the "CRANK ATTACH ADJUST" and the "ADJUSTED IN/OUT POSITION." The parameter value of the "IN/OUT CLEAT POSITION" is measured using the transverse position scale 56b as illustrated in FIG. 13. The parameter value of the "CRANK ATTACH ADJUST" is determined by the parameter value of the "SHOES-CLEAT ANGLE" and the second parameter chart 36 as illustrated in FIG. 17. The second parameter chart 36 provides the parameter values of the "CRANK ATTACH ADJUST" corresponding to different parameter values of the "SHOES-CLEAT ANGLE." The parameter values of the "CRANK ATTACH ADJUST" in the second parameter chart 36 are predetermined such that the parameter values of the "CRANK ATTACH ADJUST" compensates the transverse displacements of the cleat 12 due to the angular displacements (e.g., "SHOES-CLEAT ANGLE") of the cleat 12 with respect to the bicycle shoe 14. The parameter value of the "ADJUSTED IN/OUT POSITION" is also determined by the parameter value of the "SHOES-CLEAT ANGLE." In particular, if the parameter value of the "SHOES-CLEAT ANGLE" is smaller than "3" degrees, then the parameter value of the "ADJUSTED IN/OUT POSITION" is set to "0." On the other hand, if the parameter value of the "SHOES-CLEAT ANGLE" is equal to or greater than "3" degrees, then the parameter value of the "ADJUSTED IN/OUT POSITION" is set to "−4."

For example, as illustrated in FIG. 17, the parameter value of the "IN/OUT CLEAT POSITION" is measured as "6." Furthermore, the parameter value of the "CRANK ATTACH ADJUST" is determined as "1.6" when the parameter value of the "SHOES-CLEAT ANGLE" is calculated as "3." Moreover, the parameter value of the "ADJUSTED IN/OUT POSITION" is set to "−4" when the parameter value of the "SHOES-CLEAT ANGLE" is calculated as "3." Thus, the parameter value of the "NOMAL/LONG AXLE" is calculated as "3.6." Then, the parameter value of the "NOMAL/LONG AXLE" is written down in the left parameter table 30L as illustrated in FIG. 17.

Figure 18:
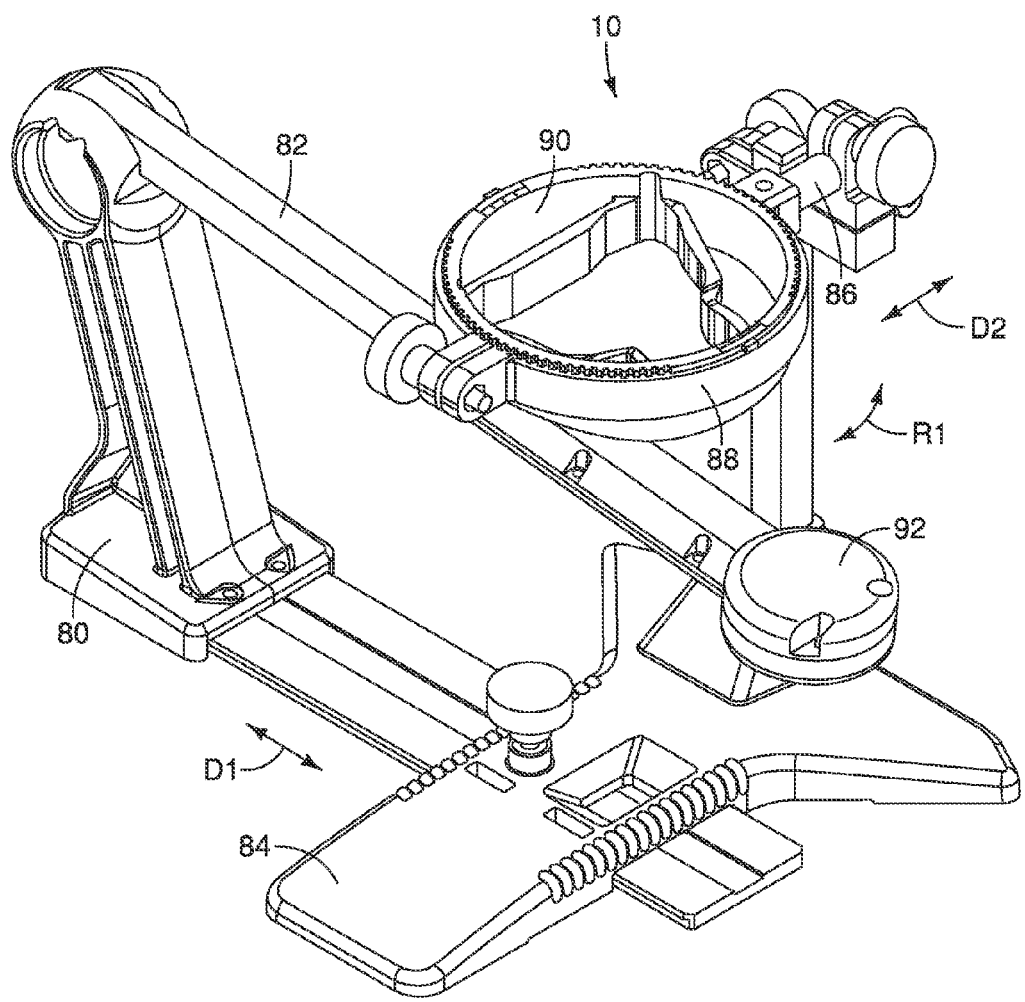
FIG. 18 is a perspective view of the cleat setting device illustrated in FIG. 1.

Furthermore, as illustrated in FIG. 18, the bicycle cleat positioning method further includes adjusting the cleat 12 with respect to the bicycle shoe 14 based on the parameter values of the "SHOES-CLEAT ANGLE," the "F/R ADJUSTED POSITION," and the "NOMAL/LONG AXLE" using the cleat setting device 10. In particular, as illustrated in FIG. 18, the cleat setting device 10 includes a base component 80 with a shoe holder 82, a lengthwise slide component 84, a widthwise slide component 86 with an attachment portion 88, and a cleat holder 90. The shoe holder 82 of the base component 80 further has an expandable toe part 92. The shoe holder 82 is disposed inside the bicycle shoe 14 to hold the bicycle shoe 14 with respect to the cleat setting device 10. The lengthwise slide component 84 is slidably coupled to the base component 80 along the lengthwise direction D1 of the bicycle shoe 14. The widthwise slide component 86 is slidably coupled to the lengthwise slide component 84 along the widthwise direction D2 of the bicycle shoe 14. The cleat holder 90 is rotatably coupled to the attachment portion 88 of the widthwise slide component 86 in the rotational direction R1 about a center of the attachment portion 88. The base component 80 further has a lengthwise scale indicative of a lengthwise position of the cleat holder 90 with respect to the shoe holder 82. The widthwise slide component 86 further has a widthwise scale indicative of a widthwise position of the cleat holder 90 with respect to the shoe holder 82. The attachment portion 88 further has an angular scale indicative of a rotational orientation of the cleat holder 90.

When the bicycle shoe 14 is mounted to the shoe holder 82 and the cleat 12 is mounted to the cleat holder 90, the lengthwise slide component 84 and the widthwise slide component 86 are adjusted to a reference cleat attachment position on the shoe sole 16 of the bicycle shoe 14 that corresponds to the reference point P15 represented by the reference slits 52a and 52b as illustrated in FIG. 13. Furthermore, the cleat holder 90 is adjusted to a reference orientation with respect to the attachment portion 88 such that the angular scale indicates "0" degree. The reference orientation corresponds to a cleat orientation represented by the reference apertures 54a, 54b and 54c as illustrated in FIG. 13. Then, the lengthwise slide component 84 is slidably adjusted in the lengthwise direction D1 by the distance indicated by the parameter value of the "F/R ADJUSTED POSITION" using the lengthwise scale of the base component 80. Furthermore, the widthwise slide component 86 is slidably adjusted in the widthwise direction D2 by the distance indicated by the parameter value of the "NOMAL/LONG AXLE" using the widthwise scale of the widthwise scale of the widthwise slide component 86. Moreover, the cleat holder 90 is rotatably adjusted in the rotational direction R1 such that the angular scale of the attachment portion 88 indicates the parameter value of the "SHOES-CLEAT ANGLE." After adjusting the cleat 12 with respect to the shoe sole 16 of the bicycle shoe 14 using the cleat setting device 10, the cleat 12 is fastened to the shoe sole 16 of the bicycle shoe 14 with screws.

As described above, the bicycle cleat positioning method applied to the person's left foot FL as illustrated in FIGS. 11 to 18 are also applied to the person's right foot FR in a similar manner, except for using the foot measuring instrument 22 by turning over the foot measuring instrument 22 or using an additional foot measuring instrument utilized for the right foot FR. Then, the cleat 12 is adjusted with respect to the bicycle shoe 14 based on the parameter values of the "SHOES-CLEAT ANGLE," the "F/R ADJUSTED POSITION," and the "NOMAL/LONG AXLE" in the right parameter table 30R for the right foot FR through the bicycle cleat positioning method as illustrated in FIGS. 11 to 18.

In this embodiment, the bicycle cleat positioning kit includes the foot locating instrument 20 made of a sheet member as illustrated in FIGS. 2 and 8. Furthermore, in this embodiment, the bicycle cleat positioning method includes manually tracing the foot outlines L10 of the person's feet FL and FR on the foot locating instrument 20 and manually determining the center lines L11, the center points P10 and the heel center positions P12 of the foot outlines L10 of the person's feet FL and FR. On the other hand, additionally or alternatively, the bicycle cleat positioning kit can also include a foot scan system or a pedograph that automatically traces and provides the foot outlines L10 of the person's feet FL and FR by sensing foot pressure from the person's feet FL and FR. Furthermore, the foot scan system or the pedograph can also automatically determine the center lines L11, the center points P10 and the heel center positions P12 of the foot outlines L10 of the person's feet FL and FR based on the foot outlines L10.

Second Embodiment

Referring now to FIGS. 19 to 26, a bicycle cleat positioning method in accordance with a second embodiment will now be explained.

In view of the similarity between the first and second embodiments, the parts of the second embodiment that are identical to the parts of the first embodiment will be given the same reference numerals as the parts of the first embodiment. In any event, the descriptions of the parts of the second embodiment that are substantially identical to the parts of the first embodiment may be omitted for the sake of brevity. However, it will be apparent to those skilled in the art from this disclosure that the descriptions and illustrations of the first embodiment also apply to this second embodiment, except as discussed and/or illustrated herein.

The bicycle cleat positioning method in accordance with the second embodiment basically includes the bicycle cleat positioning method described with reference to FIGS. 7 to 15 in accordance with the first embodiment. In other words, the foot outlines L10, the center lines L11, the transverse lines L12, and the center point P10 as illustrated in FIG. 8, the circular marks M11, M12 and M13 as illustrated in FIG. 13, and the parameter values of the "FOOT OPEN ANGLE" and the "SHOES-CLEAT ANGLES" of the left and right parameter tables 30L and 30R as illustrated in FIG. 15 are already obtained through the bicycle cleat positioning method as illustrated in FIGS. 7 to 15 before the bicycle cleat positioning method as illustrated in FIGS. 19 to 26. The bicycle cleat positioning method as illustrated in FIG. 19 to 26 utilizes the cleat adjusting instrument 24 for adjusting the cleat 12 with respect to the shoe sole 16 of the bicycle shoe 14 instead of utilizing the cleat setting device 10. Hereinafter, the bicycle cleat positioning method applied to the person's left foot FL is identical to the bicycle cleat positioning method applied to the person's right foot FR. Thus, only the bicycle cleat positioning method applied to the person's left foot FL will be discussed herein for the sake of brevity.

Figure 19:
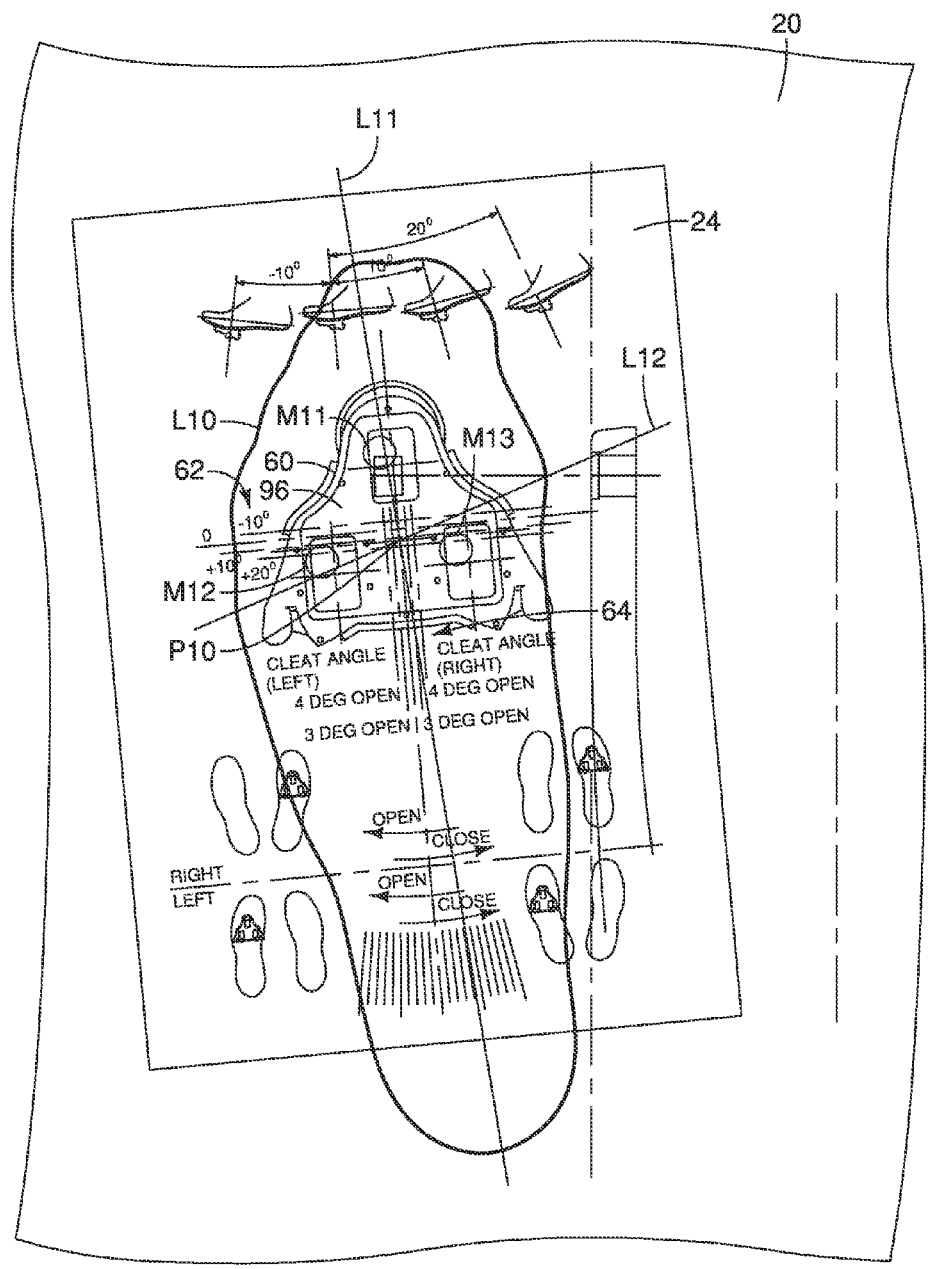
FIG. 19 is a top plan view of the foot locating instrument illustrated in FIG. 2 and the cleat adjusting instrument illustrated in FIG. 4 in accordance with a second embodiment, illustrating the cleat adjusting instrument overlaid on the foot locating instrument.

As illustrated in FIG. 19, the bicycle cleat positioning method includes providing an attachment sheet 96 to the cleat adjusting instrument 24. The attachment sheet 96 is preferably made of a transparent or translucent sticker. The attachment sheet 96 is detachably disposed on the cleat reference indicator 60 on the cleat adjusting instrument 24. The attachment sheet 96 is disposable and replaceable after tracing the circular marks M11, M12 and M13 on the attachment sheet 96.

Furthermore, as illustrated in FIGS. 19 to 23, the bicycle cleat positioning method includes overlying the cleat adjusting instrument 24 on the foot locating instrument 20, adjusting the cleat adjusting instrument 24 with respect to the circular marks M11, M12 and M13 (e.g., cleat attachment locations) that has been provided on the foot locating instrument 20, and tracing the circular marks M11, M12 and M13 on the cleat adjusting instrument 24.

Figure 20:
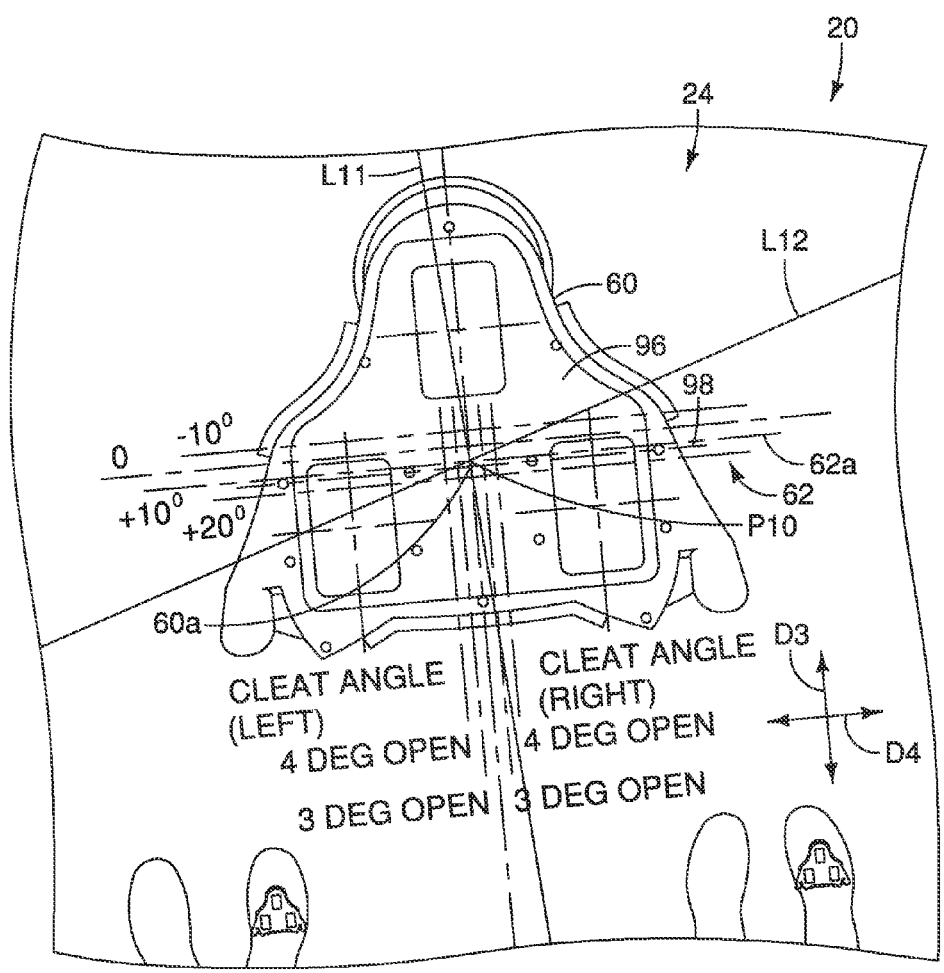
FIG. 20 is an enlarged view of the cleat adjusting instrument illustrated in FIG. 4, illustrating the cleat adjusting instrument aligned to the center point of the foot outline of the person's foot on the foot locating instrument in a lengthwise direction of the cleat adjusting instrument.
Figure 21:
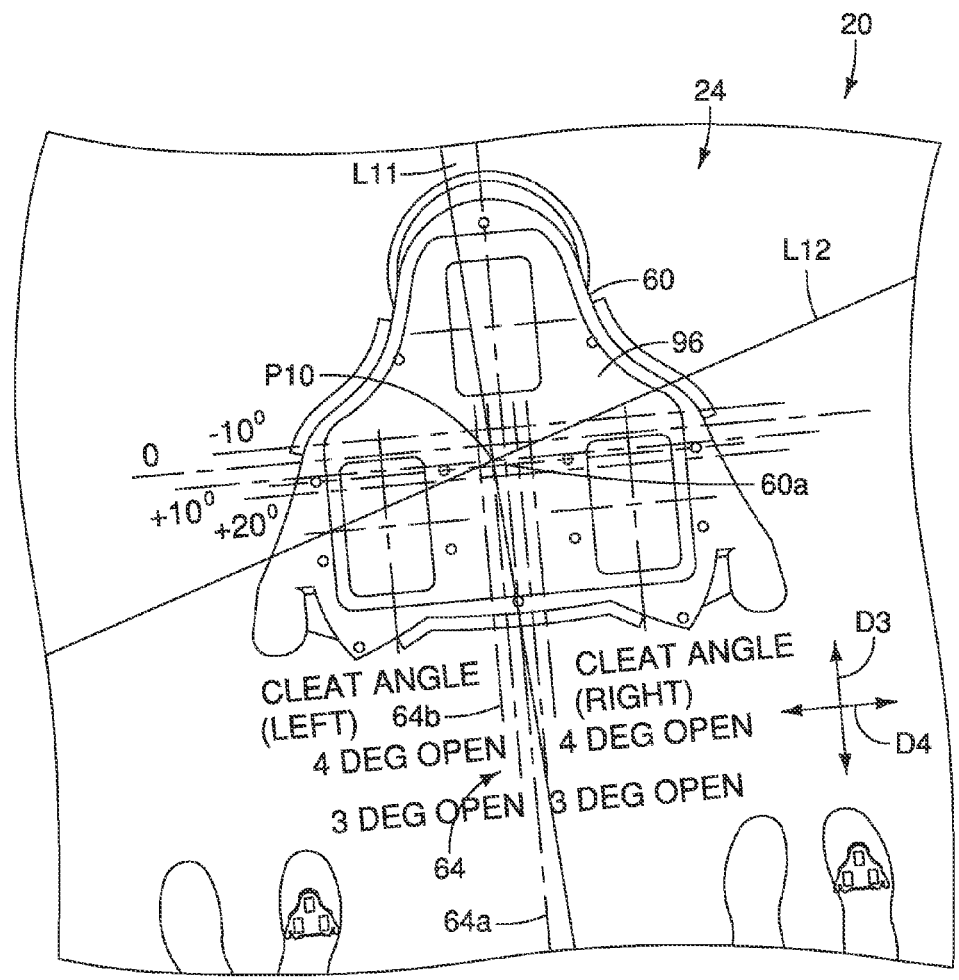
FIG. 21 is an enlarged view of the cleat adjusting instrument illustrated in FIG. 4, illustrating the cleat adjusting instrument aligned to the center point of the foot outline of the person's foot on the foot locating instrument in a widthwise direction of the cleat adjusting instrument.

Specifically, after the cleat adjusting instrument 24 is overlaid on the foot locating instrument 20, the lengthwise position alignment indicators 62 and the widthwise position alignment indicators 64 are aligned to the center point P10 of the foot outline L10 as illustrated in FIGS. 19 to 21.

First, as illustrated in FIG. 20, the cleat reference indicator 60 is adjusted in the lengthwise direction D3 using the lengthwise position alignment indicators 62. The lengthwise position alignment indicators 62 are provided corresponding different pedaling angles. Specifically, as illustrated in FIG. 20, four lengthwise position alignment indicators 62 are provided corresponding to different pedaling angles of "−10," "0," "+10" and "+20," respectively. The pedaling angle is determined by the foot posture of the person's foot while pedaling. For example, the person or the cleat fitter who adjusts the cleat 12 to the bicycle shoe 14 observes the foot posture of the person's foot while pedaling, and determines the pedaling angle from alternatives ("−10," "0," "10" and "20") with reference to a graphic diagram on the cleat adjusting instrument 24. The graphic diagram is the same as the graphic diagram 32 (see FIG. 2, for example). The cleat reference indicator 60 is adjusted with respect to the foot locating instrument 20 in the lengthwise direction D3 such that the center point P10 on the foot locating instrument 20 is aligned to one of the lengthwise position alignment indicators 62 that corresponds to determined pedaling angle. The lengthwise position alignment indicators 62 are arranged with respect to a lengthwise reference indicator 98 such that distances between the lengthwise position alignment indicators 62 and the lengthwise reference indicator 98 correspond to the parameter values of the "PEDALING ADJUST" in the first parameter chart 34 in FIG. 16, respectively. The lengthwise reference indicator 98 represents a lengthwise position of a cleat attachment reference position 60a of the cleat reference indicator 60. Furthermore, the lengthwise position alignment indicators 62 corresponding to the parameter values of "−10," "0" and "+10" are located on a toe side of the foot outline L10 in the lengthwise direction D3 with respect to the lengthwise reference indicator 98 such that the cleat reference indicator 60 is adjusted toward a heel side of the foot outline L10 in the lengthwise direction D3 when the center point P10 is located on one of the lengthwise position alignment indicators 62 corresponding to the parameter values of "−10," "0" and "+10." On the other hand, the lengthwise position alignment indicator 62 corresponding to the parameter value of "+20" is located on the heel side of the foot outline L10 in the lengthwise direction D3 with respect to the lengthwise reference indicator 98 such that the cleat reference indicator 60 is adjusted toward the toe side of the foot outline L10 in the lengthwise direction D3 when the center point P10 is located on the lengthwise position alignment indicator 62 corresponding to the parameter value of "+20."

For example, as illustrated in FIG. 20, the cleat reference indicator 60 is adjusted with respect to the foot locating instrument 20 in the lengthwise direction D3 such that the center point P10 on the foot locating instrument 20 is aligned to a lengthwise position alignment indicator 62a corresponding to the pedaling angle of "+10" when the determined pedaling angle is "+10."

Next, as illustrated in FIG. 21, the cleat reference indicator 60 is adjusted in the widthwise direction D4 using the widthwise position alignment indicators 64. The widthwise position alignment indicators 64 are provided corresponding different cleat angles with respect to the bicycle shoe 14. Specifically, as illustrated in FIG. 21, five widthwise position alignment indicators 64 are provided corresponding to different parameter values of the "SHOES-CLEAT ANGLE" in left and right parameter tables 30L and 30R. In particular, two of the widthwise position alignment indicators 64 are provided corresponding to the cleat angles of "3" and "4" for the left foot FL, and two of the widthwise position alignment indicators 64 are provided corresponding to the cleat angles of "3" and "4" for the right foot FR. One widthwise position alignment indicator 64a is provided corresponding to the cleat angles less than "3" degrees for the left and right feet FL and FR. The widthwise position alignment indicator 64a passes through the cleat attachment reference position 60a of the cleat reference indicator 60 and represents a widthwise position of the cleat attachment reference position 60a of the cleat reference indicator 60. The parameter value of the "SHOES-CLEAT ANGLE" is calculated as explained with reference to FIG. 15. Then, the cleat reference indicator 60 is adjusted with respect to the foot locating instrument 20 in the widthwise direction D4 such that the center point P10 on the foot locating instrument 20 is aligned to one of the widthwise position alignment indicators 64 that corresponds to the determined parameter value of the "SHOES-CLEAT ANGLE." The widthwise position alignment indicators 64 are arranged such that distances between the widthwise position alignment indicators 64 and the cleat attachment reference position 60a in the widthwise direction D4 correspond to the parameter values of the "CRANK ATTACH ADJUST" in the second parameter chart 36 in FIG. 17, respectively. Furthermore, two of the widthwise position alignment indicators 64 for the left foot FL are located on a left side of the widthwise position alignment indicator 64a in the widthwise direction D4 such that the cleat reference indicator 60 is inwardly adjusted towards the left crank arm reference indicators 28L in the widthwise direction D4 when the center point P10 is located on one of the widthwise position alignment indicators 64 for the left foot FL. On the other hand, two of the widthwise position alignment indicators 64 for the right foot FR are located on a right side of the widthwise position alignment indicator 64a in the widthwise direction D4 such that the cleat reference indicator 60 is inwardly adjusted toward the right crank arm reference indicator 28R in the widthwise direction D4 when the center point P10 is located on one of the widthwise position alignment indicators 64 for the right foot FR.

For example, as illustrated in FIG. 21, the cleat reference indicator 60 is adjusted with respect to the foot locating instrument 20 in the widthwise direction D4 such that the center point P10 on the foot locating instrument 20 is aligned to a widthwise position alignment indicator 64b corresponding to the cleat angle of "3" degrees when the determined parameter value of the "SHOES-CLEAT ANGLE" in the left parameter table 30L is "3" degrees. While the cleat reference indicator 60 is adjusted with respect to the foot locating instrument 20 in the widthwise direction D4, the center point P10 is stayed on one of the lengthwise position alignment indicators 62.

Figure 22:
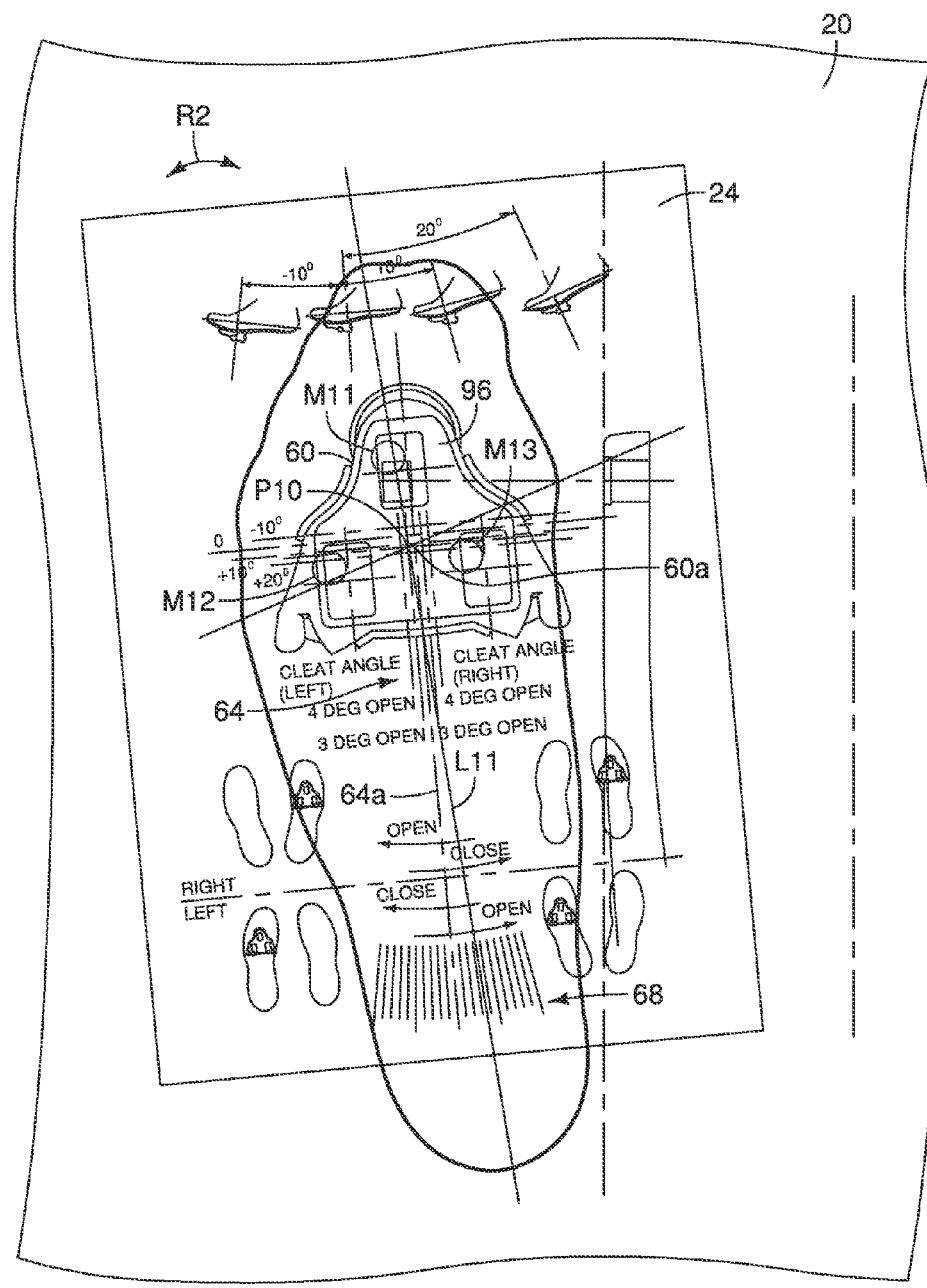
FIG. 22 is an enlarged top plan view of the foot locating instrument illustrated in FIG. 2 and the cleat adjusting instrument illustrated in FIG. 4, illustrating an angular adjustment of the cleat adjusting instrument with respect to the center line of the foot outline of the person's foot on the foot locating instrument.

Furthermore, as illustrated in FIG. 22, the cleat reference indicator 60 is further rotated in a rotational direction R2 about the cleat attachment reference position 60a of the cleat reference indicator 60 such that the cleat orientation alignment indicator 68 is aligned with respect to the center line L11 of the foot outline L10. In particular, the cleat reference indicator 60 is rotated about the cleat attachment reference position 60a such that the center line L11 of the foot outline L10 and the widthwise position alignment indicator 64a that passes through the cleat attachment reference position 60a form an angle corresponding to the parameter value of the "FOOT OPEN ANGLE" in the left parameter table 30L.

For example, as illustrated in FIG. 22, the cleat reference indicator 60 is rotated about the cleat attachment reference position 60a of the cleat reference indicator 60 such that the center line L11 of the foot outline L10 and the widthwise position alignment indicator 64a form an angle of "6" degrees when the parameter value of the "FOOT OPEN ANGLE" in the left parameter table 30L is "6."

Figure 23:
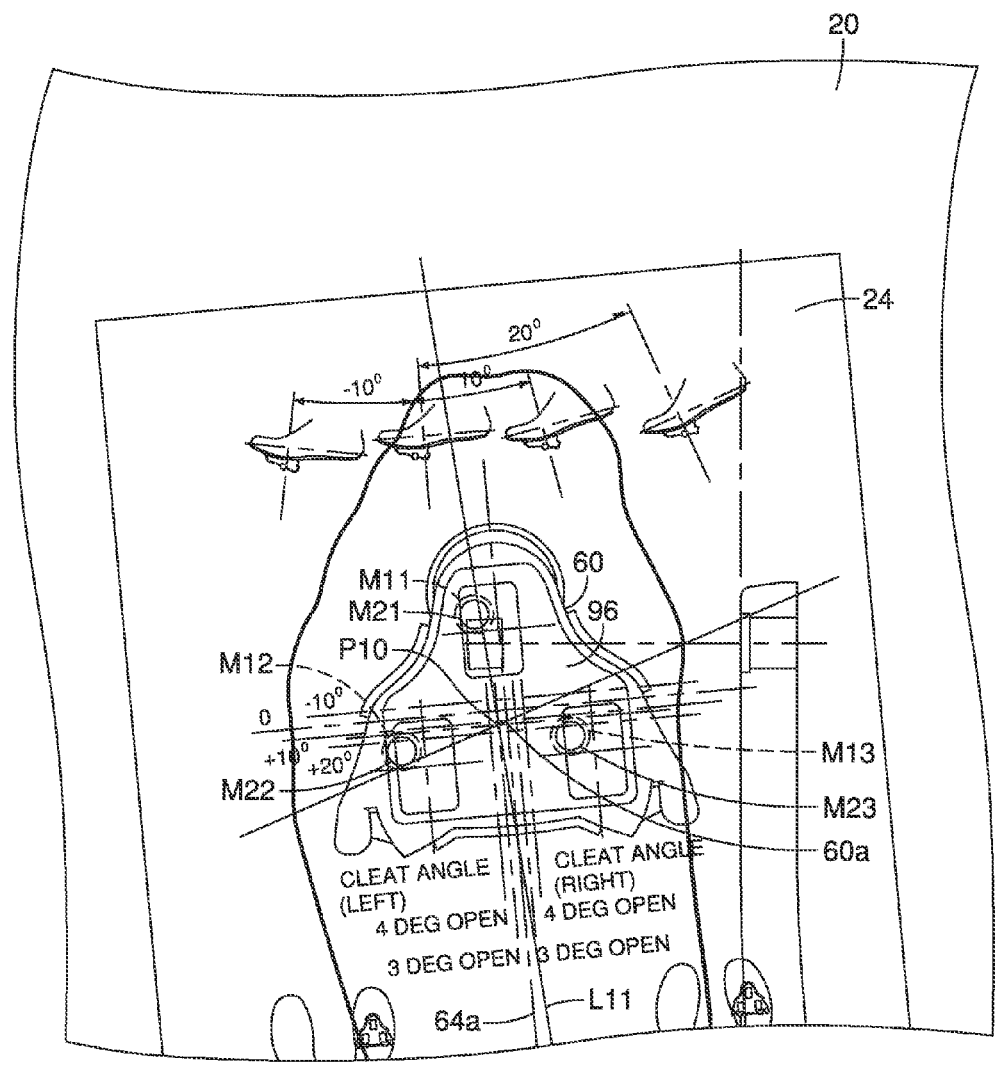
FIG. 23 is an enlarged view of the cleat adjusting instrument illustrated in FIG. 4, illustrating a tracing of circular marks on the cleat adjusting instrument.

With the procedures explained with reference to FIGS. 20 to 22, the cleat adjusting instrument 24 is adjusted with respect to the circular marks M11, M12 and M13 that have been provided on the foot locating instrument 20. Next, as illustrated in FIG. 23, the circular marks M11, M12 and M13 are traced on the cleat adjusting instrument 24. Specifically, the circular marks M11, M12 and M13 are traced on the attachment sheet 96 of the cleat adjusting instrument 24 as circular marks M21, M22 and M23, respectively.

Figure 24:
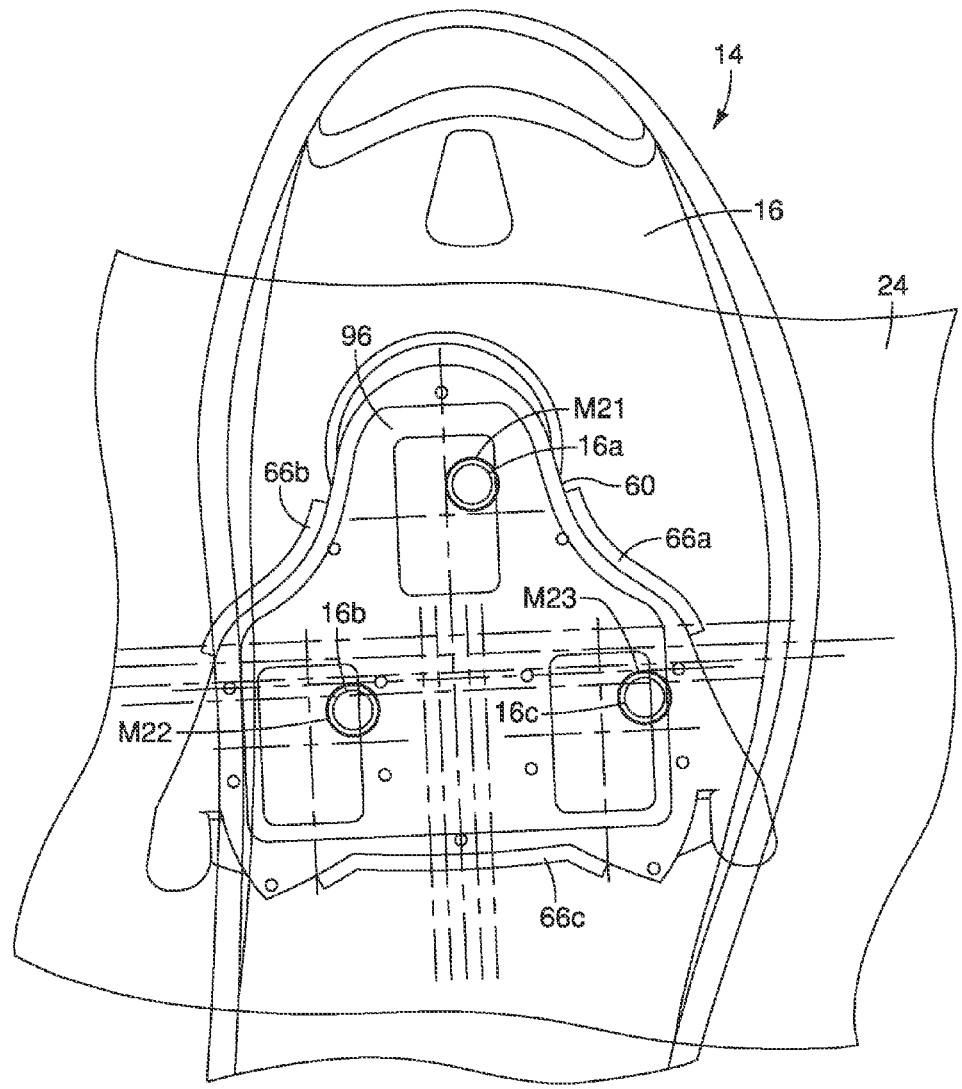
FIG. 24 is an enlarged bottom plan view of the bicycle shoe, illustrating the cleat adjusting instrument overlaid on the shoe sole of the bicycle shoe such that the circular marks traced on the cleat adjusting instrument are aligned to cleat attachment holes of the shoe sole of the bicycle shoe, respectively.

Furthermore, as illustrated in FIG. 24, the bicycle cleat positioning method further includes aligning the circular marks M21, M22 and M23 on the attachment sheet 96 of the cleat adjusting instrument 24 to cleat attachment holes 16a, 16b and 16c on the shoe sole 16 of the bicycle shoe 14, respectively. Specifically, the cleat adjusting instrument 24 is turned over, and placed on the shoe sole 16 of the bicycle shoe 14. Then, the circular marks M21, M22 and M23 on the attachment sheet 96 of the cleat adjusting instrument 24 are aligned to the cleat attachment holes 16a, 16b and 16c on the shoe sole 16 of the bicycle shoe 14, respectively.

Figure 25:
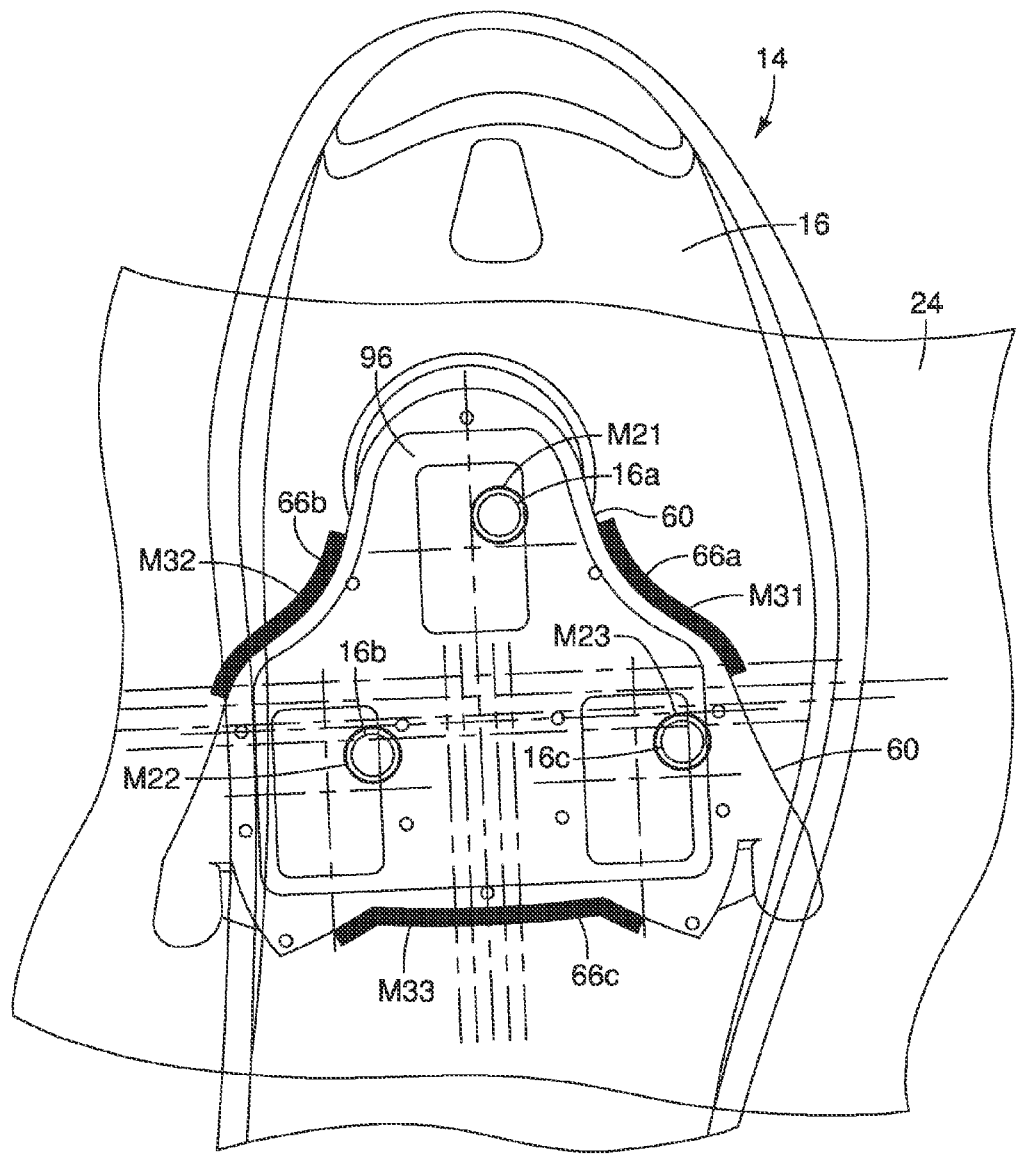
FIG. 25 is an enlarged bottom plan view of the bicycle shoe, illustrating a marking of the shoe sole of the bicycle shoe with positioning marks using the cleat adjusting instrument.
Figure 26:
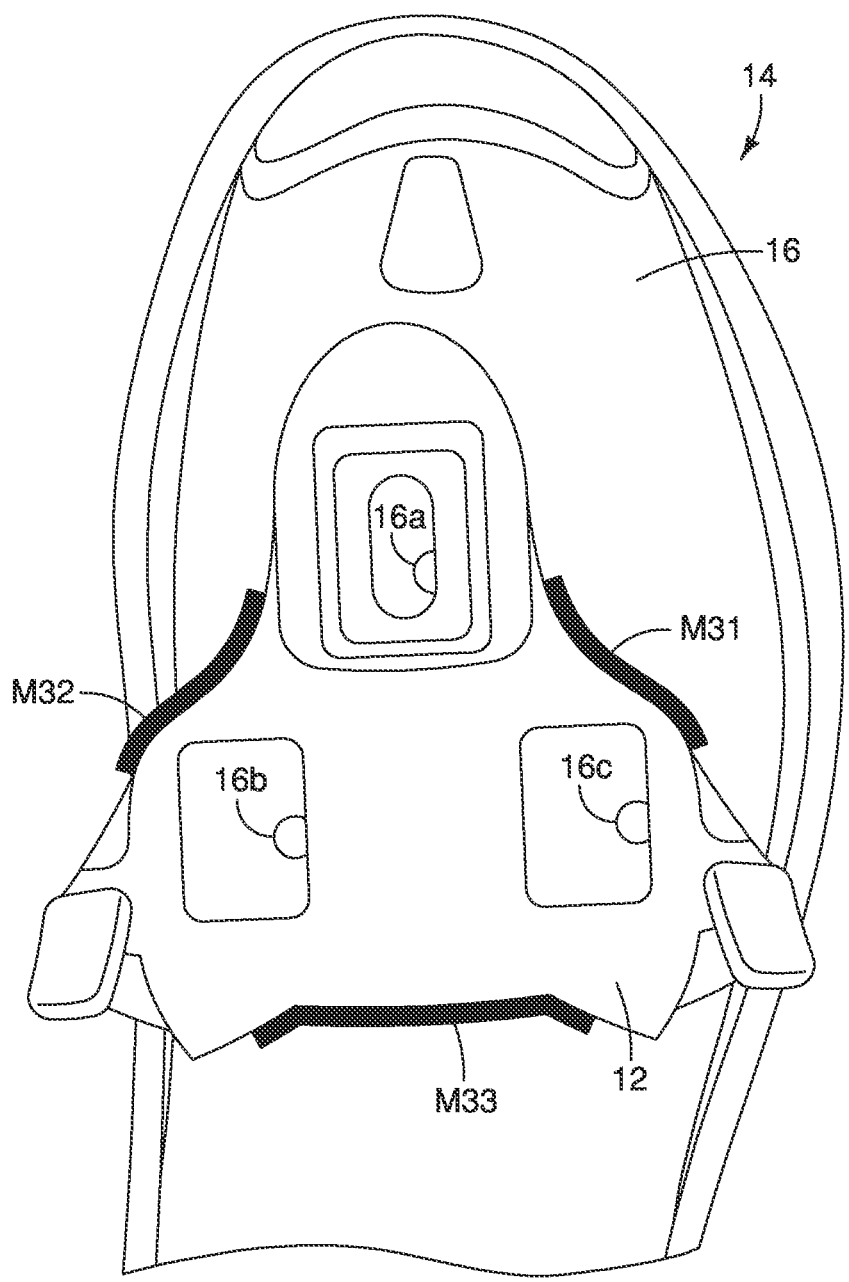
FIG. 26 is an enlarged bottom plan view of the bicycle shoe, illustrating the cleat aligned to the positioning marks provided on the shoe sole of the bicycle shoe.

Moreover, as illustrated in FIG. 25, the bicycle cleat positioning method further includes marking the shoe sole 16 of the bicycle shoe 14 with a plurality of positioning marks M31, M32 and M33 (e.g., cleat outline points) through the positioning slits 66a, 66b and 66c of the cleat adjusting instrument 24, respectively. Then, as illustrated in FIG. 26, the cleat 12 is adjusted with respect to the positioning marks M31, M32 and M33 on the shoe sole 16 of the bicycle shoe 14. Specifically, the cleat 12 is adjusted such that an outline of the cleat 12 is aligned to the positioning marks M31, M32 and M33, respectively. After adjusting the cleat 12 with respect to the shoe sole 16 of the bicycle shoe 14, the cleat 12 is fastened to the shoe sole 16 of the bicycle shoe 14 with screws. If the determined position of the cleat 12 indicated by the positioning marks M31, M32 and M33 is outside an adjustable range of the cleat 12 with respect to the shoe sole 16 of the bicycle shoe 14, then the cleat 12 can be further adjusted to a position within the adjustable range that is closest to the determined position of the cleat 12, and fastened to the shoe sole 16 of the bicycle shoe 14.

The bicycle cleat positioning method applied to the person's left foot FL as illustrated in FIGS. 19 to 26 are also applied to the person's right foot FR in a similar manner.

With the bicycle cleat positioning kit and the bicycle cleat positioning method, the cleats 12 can be adjusted with respect to the bicycle shoes 14 such that the cleats 12 are located vertically blow the center points of the person's feet FL and FR while pedaling.

Third Embodiment

Referring now to FIGS. 27 to 36, a bicycle cleat positioning kit in accordance with a third embodiment will now be explained.

In view of the similarity between the first and third embodiments, the descriptions of the parts of the third embodiment that are substantially identical to the parts of the first embodiment may be omitted for the sake of brevity. However, it will be apparent to those skilled in the art from this disclosure that the descriptions and illustrations of the first embodiment also apply to this third embodiment, except as discussed and/or illustrated herein.

Figure 30:
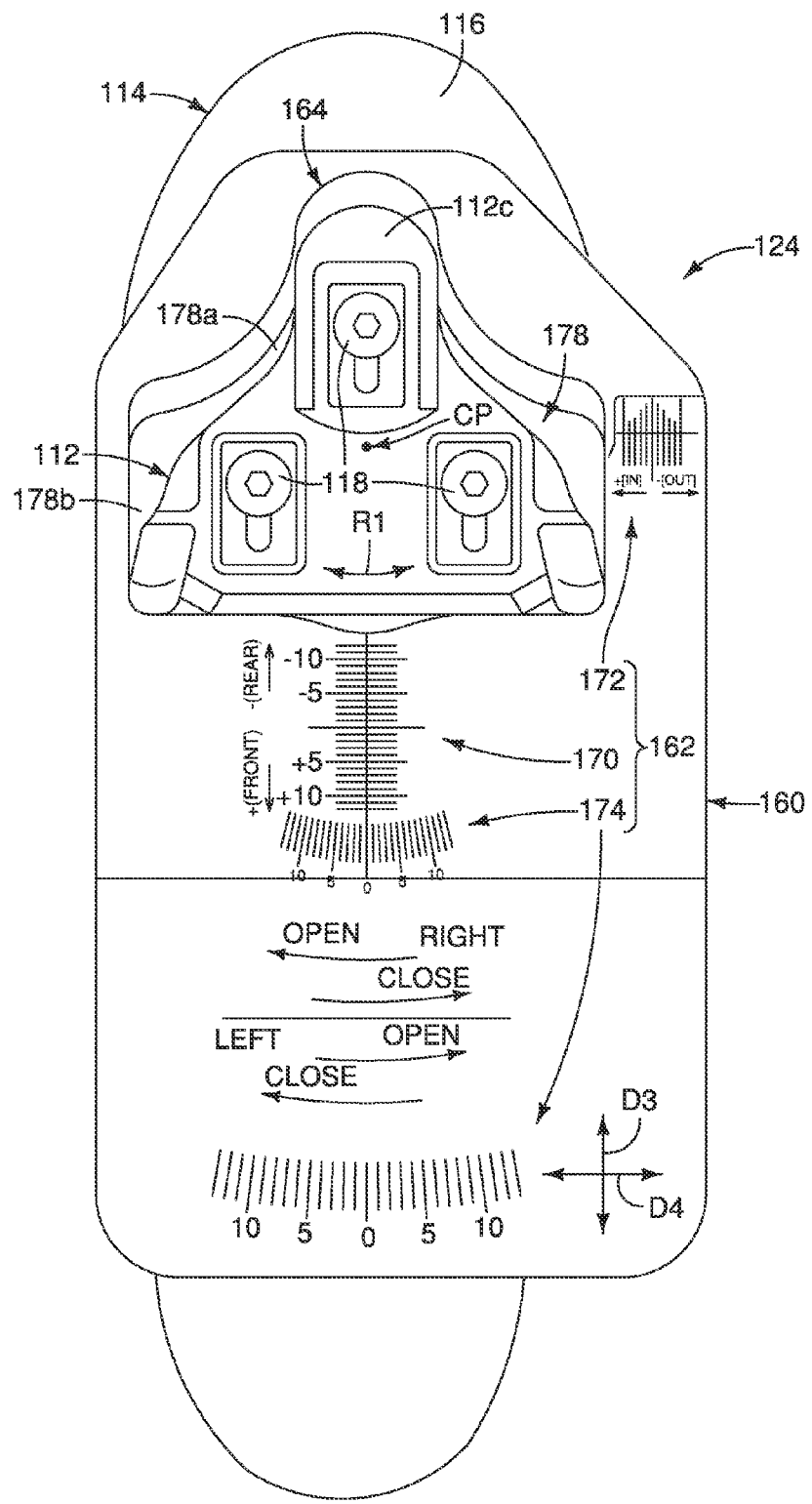
FIG. 30 is a top plan view of the cleat adjusting instrument illustrated in FIG. 29, with a cleat attached to the cleat adjusting instrument while the cleat is adjustably attached to a bicycle shoe.
Figure 31:
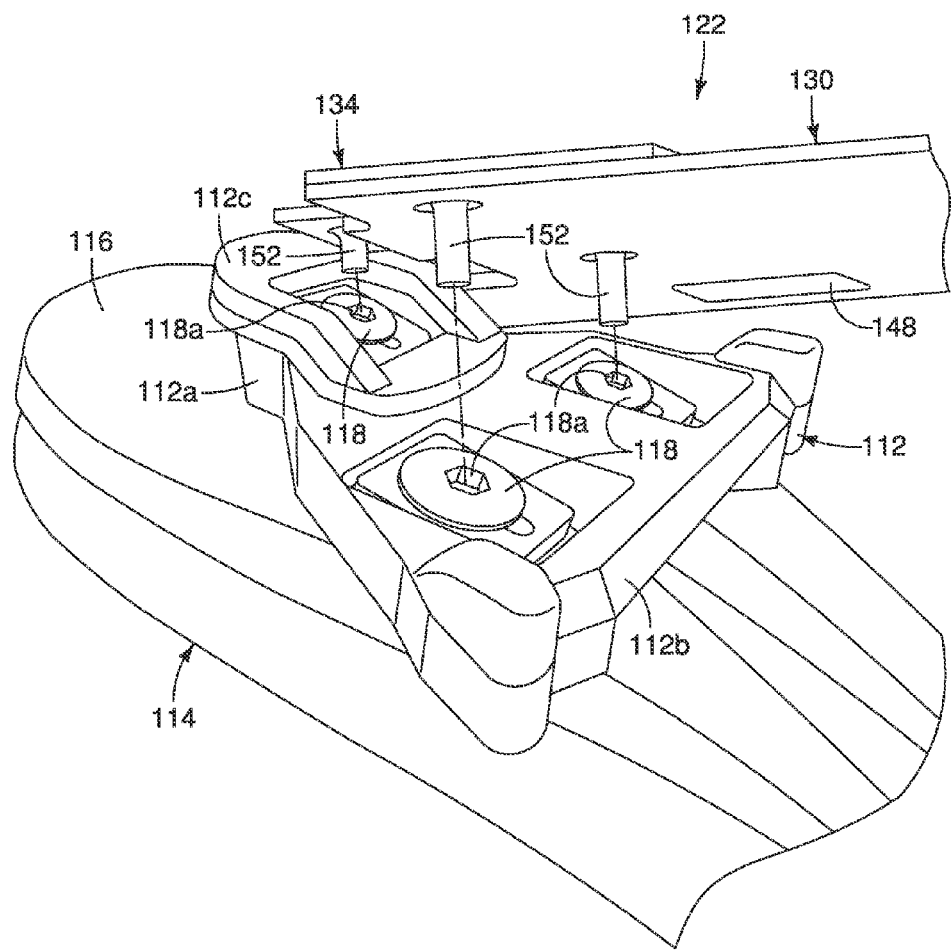
FIG. 31 is a perspective view of the reference indicating instrument illustrated in FIG. 27, illustrating an attachment of the reference indicating instrument to the bicycle shoe.
Figure 32:
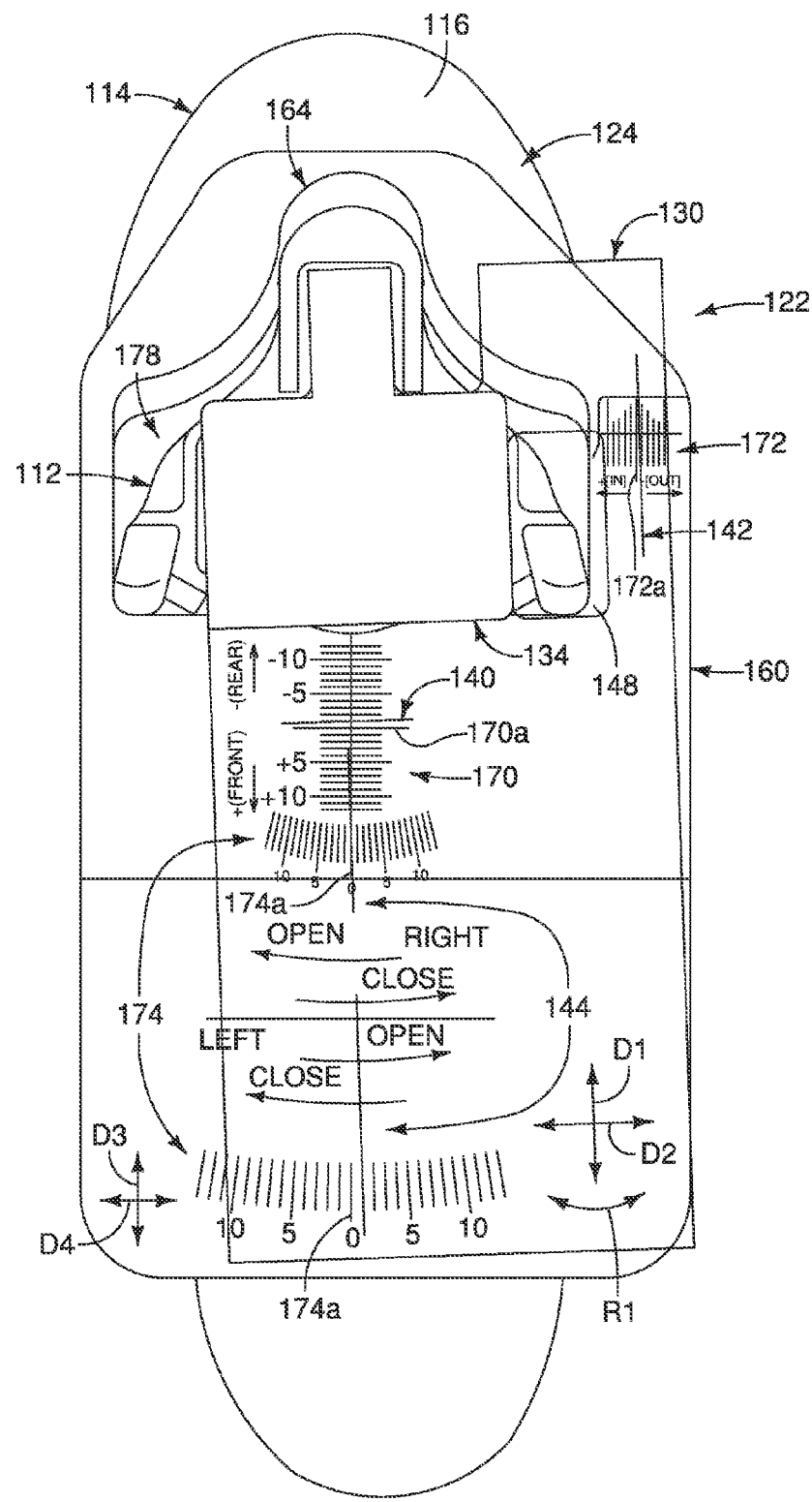
FIG. 32 is a top plan view of the reference indicating instrument illustrated in FIG. 27 and the cleat adjusting instrument illustrated in FIG. 29, illustrating the reference indicating instrument attached to the bicycle shoe while the cleat adjusting instrument is attached to the cleat.

As best shown in FIGS. 30 to 32, the bicycle cleat positioning kit in accordance with the third embodiment is utilized for adjusting a cleat 112 with respect to a shoe sole 116 of a bicycle shoe 114 without utilizing the cleat setting device 10 shown in FIG. 18. The cleat 112 and the bicycle shoe 114 are substantially identical to the cleat 12 and the bicycle shoe 114, and can include conventional structures. Thus, the descriptions of the cleat 112 and the bicycle shoe 114 are omitted for the sake of brevity. Although the cleat 112 is shown as a cleat conventionally used for road bikes in the illustrated embodiment, the cleat 112 can also be a cleat conventionally used for mountain bikes. Similarly, the bicycle shoe 114 is shown as a road bike shoe in the illustrated embodiment, the bicycle shoe 114 can also be a mountain bike shoe. The cleat 112 is fixedly coupled to the shoe sole 116 of the bicycle shoe 114 with a plurality of (three in this embodiment) cleat fasteners 118 (e.g., cleat fixing bolt) while the cleat fasteners 118 are fully threaded into threaded holes (not shown) formed on the shoe sole 116 of the bicycle shoe 114. On the other hand, as best shown in FIGS. 30 and 31, the cleat 112 is adjustably mounted to the shoe sole 116 of the bicycle shoe 114 while the cleat fasteners 118 are temporarily threaded into the threaded holes of the bicycle shoe 114. In other words, while adjusting the cleat 112 with respect to the shoe sole 116 of the bicycle shoe 114, the cleat fasteners 118 are temporarily threaded to the threaded holes of the bicycle shoe 114.

As best shown in FIG. 32, the bicycle cleat positioning kit in accordance with the third embodiment includes a reference indicating instrument 122 and a cleat adjusting instrument or ruler 124. The reference indicating instrument 122 is non-movably attachable with respect to the bicycle shoe 114 such that the reference indicating instrument 122 provides references with respect to the bicycle shoe 114 for adjustment of the cleat 112 with respect to the bicycle shoe 114. The cleat adjusting instrument 124 is movable with the cleat 112 with respect to the bicycle shoe 114 while the reference indicating instrument 122 is stationary with respect to the bicycle shoe 114.

Figure 27:
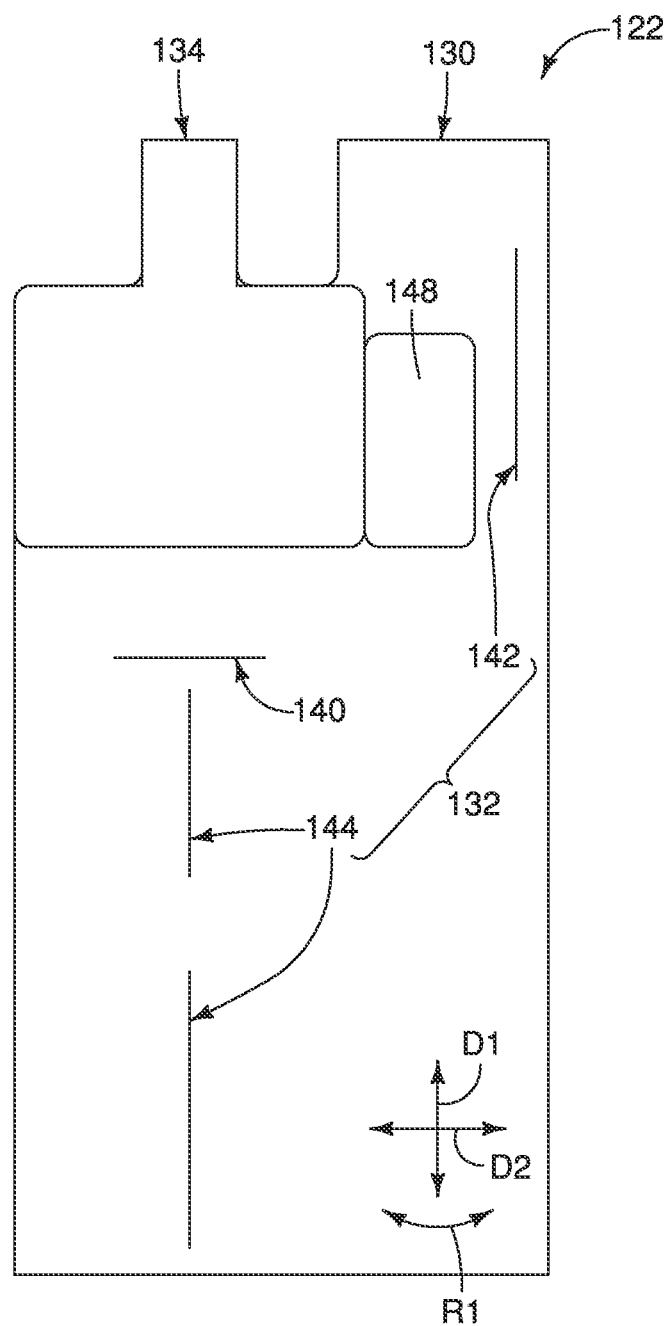
FIG. 27 is a top plan view of a reference indicating instrument of a bicycle cleat positioning kit in accordance with a third embodiment.
Figure 28:
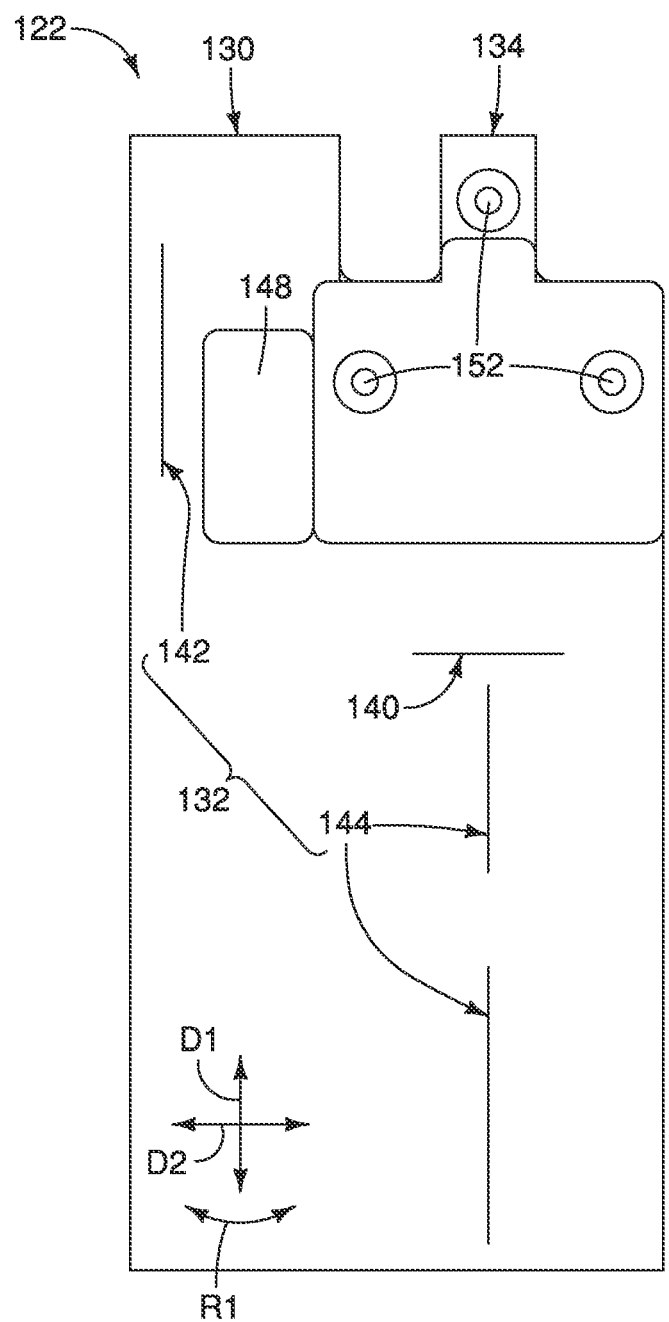
FIG. 28 is a bottom plan view of the reference indicating instrument illustrated in FIG. 27.

As illustrated in FIGS. 27 and 28, the reference indicating instrument 122 basically includes a reference indicating section 130 with a shoe reference indicator 132, and a shoe attachment section 134. The reference indicating section 130 includes a transparent or translucent sheet member on which the shoe reference indicator 132 is disposed. In particular, the reference indicating section 130 is made of a plastic material or any other suitable material. The shoe reference indicator 132 is arranged with respect to the bicycle shoe 114 while the reference indicating instrument 122 is attached to the shoe sole 116 of the bicycle shoe 114. The shoe reference indicator 132 has at least one of a longitudinal position reference line 140, a transverse position reference line 142, and a pair of orientation reference lines 144. Preferably, the shoe reference indicator 132 has all of the longitudinal position reference line 140, the transverse position reference line 142, and the orientation reference lines 144 as illustrated in FIGS. 27 and 28. The longitudinal position reference line 140, the transverse position reference line 142, and the orientation reference lines 144 form line parts (e.g., at least one line part) that represents references of the bicycle shoe 114.

In particular, the longitudinal position reference line 140 represents a longitudinal reference position of the bicycle shoe 114 in a lengthwise (or longitudinal) direction D of the bicycle shoe 114. In other words, the longitudinal position reference line 140 forms a line part that represents a first reference position of the bicycle shoe 114 in a first direction of the bicycle shoe 114. The longitudinal position reference line 140 extends in a widthwise (or transverse) direction D2 of the bicycle shoe 114. The lengthwise direction D1 and the widthwise direction D2 are perpendicular to each other. Furthermore, the transverse position reference line 142 represents a transverse reference position of the bicycle shoe 114 in the widthwise direction D2 of the bicycle shoe 114. In other words, the transverse position reference line 142 form a line part that represents a second reference position of the bicycle shoe 114 in a second direction of the bicycle shoe 114, which is perpendicular to the first direction of the bicycle shoe 114. The transverse position reference line 142 extends in the lengthwise direction D1 of the bicycle shoe 114. Moreover, the orientation reference lines 144 are aligned in the lengthwise direction D1 relative to each other, and represent a reference orientation of the bicycle shoe 114 along a rotational direction R1 of the bicycle shoe 114. The rotational direction R1 is a circumferential direction about an axis perpendicular to both the lengthwise and widthwise directions D and D2. In the illustrated embodiment, the reference orientation of the bicycle shoe 114 is parallel to the lengthwise direction D1 of the bicycle shoe 114. Thus, in the illustrated embodiment, the orientation reference lines 144 extend in the lengthwise direction D1 of the bicycle shoe 114.

Referring further to FIGS. 27 and 28, the reference indicating section 130 further has an aperture 148 that is located next to the shoe attachment section 134. The aperture 148 is arranged with respect to the shoe attachment section 134 such that a part of the cleat 112 is disposed through the aperture 148 while the reference indicating instrument 122 is attached to the bicycle shoe 114. This aperture 148 prevents the cleat 112 from interfering with and warping the reference indicating section 130 of the reference indicating instrument 122 while the reference indicating instrument 122 is attached to the bicycle shoe 114. The aperture 148 can be omitted as necessary.

The shoe attachment section 134 is fixedly attached to the reference indicating section 130 at a location adjacent to the aperture 148 of the reference indicating section 130. In particular, the shoe attachment section 134 is independently formed as a separate member from the reference indicating section 130. The shoe attachment section 134 is fixedly attached to the reference indicating section 130 with an adhesive agent or an adhesive tape. The shoe attachment section 134 can also be fixedly attached to the reference indicating section 130 in any other conventional fixing manner. The shoe attachment section 134 is made of a plastic material or any other suitable rigid material. Of course, alternatively, the shoe attachment section 134 can be integrally formed with the reference indicating section 130 as a one-piece, unitary member.

As best shown in FIG. 31, the shoe attachment section 134 of the reference indicating instrument 122 is detachably coupled to the bicycle shoe 114 while the reference indicating instrument 122 is attached to the bicycle shoe 114. The shoe attachment section 134 has at least one (three in this embodiment) projecting part 152 that mates with sockets 118a (e.g., tool engagement bore) of the cleat fasteners 118. Specifically, the projecting parts 152 are spaced apart from each other at locations corresponding to the threaded holes of the shoe sole 116 into which the cleat fasteners 118 are threaded. The projecting parts 152 have diameters that are dimensioned such that the projecting parts 152 fittedly mate with the sockets 118a of the cleat fasteners 118, respectively, without any plays in the lengthwise direction D1 and the widthwise direction D2. As illustrated in FIG. 28, the projecting parts 152 extend from the shoe attachment section 134 in a direction perpendicular to both the lengthwise direction D1 and the widthwise direction D2. The shoe attachment section 134 is attached to the reference indicating section 130 such that two of the projecting parts 152 disposed on a heel side in the lengthwise direction D1 extend through a pair of through holes on the reference indicating section 130. The two of the projecting parts 152 are aligned in the widthwise direction D2, while the other one of the projecting parts 152 disposed on a toe side in the lengthwise direction D1 is located at a midst location between the two of the projecting parts 152 in the widthwise direction D2. Furthermore, as best shown in FIG. 28, the orientation reference lines 144 and the other one of the projecting parts 152 are aligned in the lengthwise direction D1. The projecting parts 152 of the shoe attachment section 134 forms an engagement structure that is configured to be engaged with the cleat fasteners 118 fastened to the bicycle shoe 114.

Figure 29:
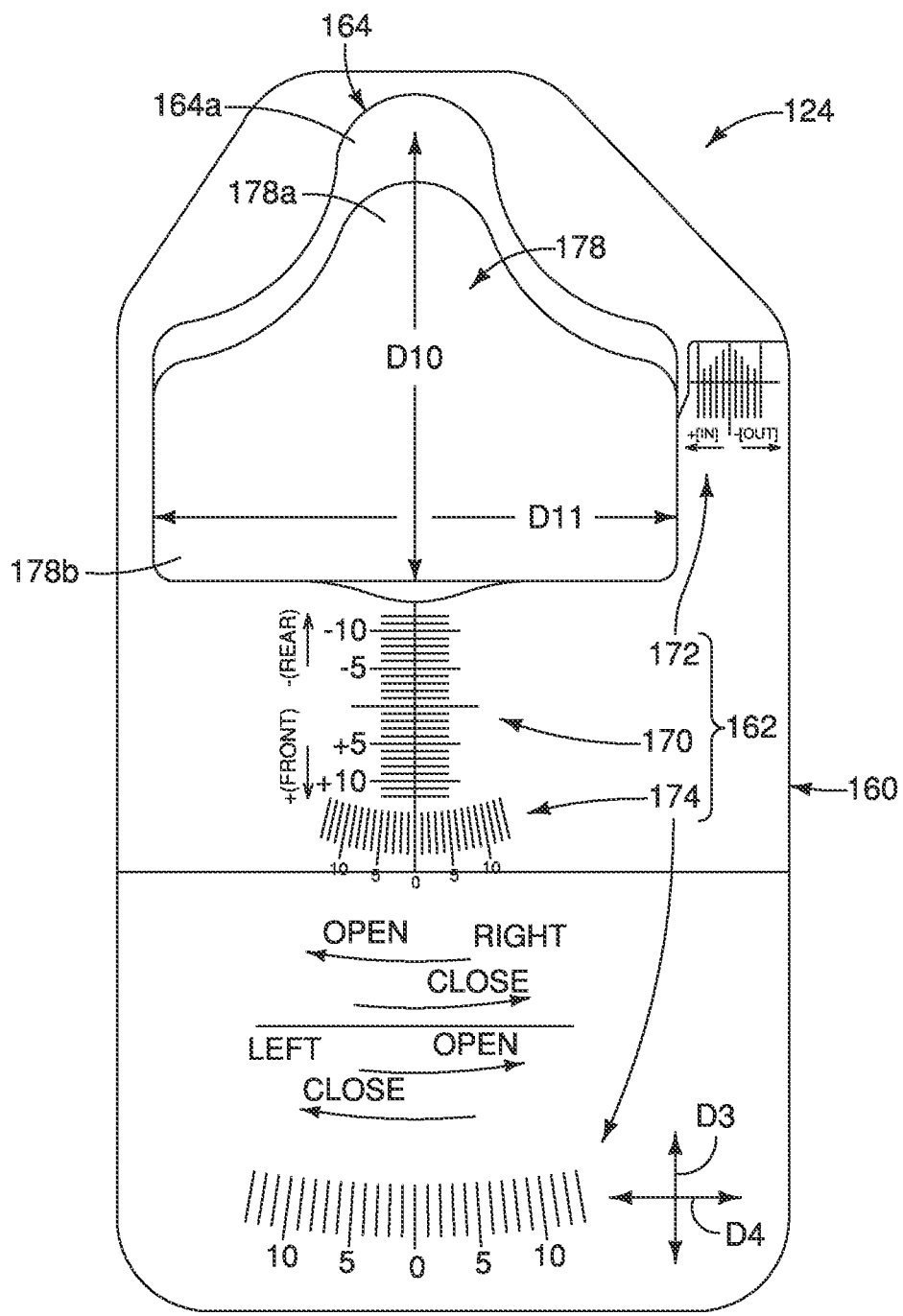
FIG. 29 is a top plan view of a cleat adjusting instrument of the bicycle cleat positioning kit in accordance with the third embodiment.

As illustrated in FIG. 30, the cleat adjusting instrument 124 is detachably attached to the cleat 112 while the cleat 112 is adjustably coupled to the bicycle shoe 114. Thus, the cleat adjusting instrument 124 is movable with the cleat 112 with respect to the bicycle shoe 114 while the cleat 112 is adjustably coupled to the bicycle shoe 114 with the cleat fasteners 118. As illustrated in FIGS. 29 and 30, the cleat adjusting instrument 124 includes a cleat adjusting section 160 with a cleat adjusting indicator 162, and a cleat attachment section 164. The cleat adjusting instrument 124 includes a rigid plate member. In particular, the cleat adjusting instrument 124 is made of a rigid plastic material or any other suitable material. The cleat adjusting instrument 124 is integrally formed as a one-piece, unitary member. The cleat adjusting indicator 162 is disposed on the cleat adjusting section 160 of the cleat adjusting instrument 124. The cleat adjusting indicator 162 is indicative of an adjustment amount of the cleat 112 with respect to the shoe reference indicator 132 of the reference indicating instrument 122. Specifically, the cleat adjusting indicator 162 has a longitudinal adjustment scale 170, a transverse adjustment scale 172, and a pair of orientation adjustment scales 174. The longitudinal adjustment scale 170, the transverse adjustment scale 172, and the orientation adjustment scales 174 form scale parts (e.g., at least one scale part) that are indicative of the adjustment amount of the cleat 112 with respect to the bicycle shoe 114.

In particular, the longitudinal adjustment scale 170 indicates a longitudinal cleat position of the cleat 112 relative to the bicycle shoe 114 in the lengthwise direction D1 of the bicycle shoe 114. In other words, the longitudinal adjustment scale 170 forms a scale part that is indicative of a first cleat position of the cleat 112 relative to the bicycle shoe 114 in a first direction of the bicycle shoe 114. Specifically, the longitudinal adjustment scale 170 has a plurality of line segments that is arranged at predetermined intervals in parallel to each other in a lengthwise direction D3 of the cleat adjusting instrument 124. In this embodiment, the line segments of the longitudinal adjustment scale 170 are arranged in the lengthwise direction D3 at 1 mm intervals. However, the value of the predetermined intervals can be different value. Furthermore, as illustrated in FIGS. 29 and 30, the longitudinal adjustment scale 170 also indicates "+(FRONT)" and "−(REAR)" directions along the lengthwise direction D3.

The transverse adjustment scale 172 indicates a transverse cleat position of the cleat 112 relative to the bicycle shoe 114 in the widthwise direction D2 of the bicycle shoe 114. In other words, the transverse adjustment scale 172 forms a scale part that is indicative of a second cleat position of the cleat 112 relative to the bicycle shoe 114 in a second direction of the bicycle shoe 114, which is perpendicular to the first direction of the bicycle shoe 114. Specifically, the transverse adjustment scale 172 has a plurality of line segments that is arranged at predetermined intervals in parallel to each other in a widthwise direction D4 of the cleat adjusting instrument 124. In this embodiment, the line segments of the transverse adjustment scale 172 are arranged in the widthwise direction D4 at 1 mm intervals. However, the value of the predetermined intervals can be different value. Furthermore, as illustrated in FIGS. 29 and 30, the transverse adjustment scale 172 also indicates "+[IN]" and "−[OUT]" directions along the widthwise direction D4.

The orientation adjustment scales 174 indicate a cleat orientation of the cleat 112 relative to the bicycle shoe 114 in the rotational direction R1 of the bicycle shoe 114. In other words, the orientation adjustment scales 174 form a scale part that is indicative of a cleat orientation of the cleat 112 relative to the bicycle shoe 114 in the rotational direction R1 of the bicycle shoe 114. Specifically, each of the orientation adjustment scales 174 has a plurality of line segments that is arranged at predetermined intervals in the rotational direction R1 of the cleat adjusting instrument 124. In this embodiment, the line segments of each of the orientation adjustment scales 174 are arranged in the rotational direction R1 at 1 degree intervals. However, the value of the predetermined intervals can be different value. The line segments of each of the orientation adjustment scales 174 extend radially with respect to a rotational center point CP of the cleat 112. Furthermore, as illustrated in FIGS. 29 and 30, the orientation adjustment scales 174 also indicates "OPEN" and "CLOSE" directions for left and right feet along the rotational direction R1 of the cleat adjusting instrument 124.

As illustrated in FIG. 30, the cleat attachment section 164 is detachably coupled to the cleat 112. Specifically, the cleat attachment section 164 has an aperture 178 that engages with the cleat 112. The cleat 112 is fittedly disposed within the aperture 178 of the cleat attachment section 164 while the cleat adjusting instrument 124 is attached to the cleat 112. The aperture 178 is configured such that the aperture 178 surrounds an outer periphery of the cleat 112. In particular, the aperture 178 has a narrow front portion 178a and a wide rear portion 178b in which a front part 112a and a rear part 112b of the cleat 112 (see also FIG. 31) are fittedly disposed, respectively. The rear portion 178b of the aperture 178 is wider than the front portion 178a of the aperture 178.

Specifically, as illustrated in FIG. 29, the aperture 178 has a lengthwise dimension D10 between front and rear inner side faces of the cleat attachment section 164. The lengthwise dimension D10 of the aperture 178 is equal to or substantially equal to a lengthwise dimension of the cleat 112 between the front and rear parts 112a and 112b of the cleat 112. Outer side faces of the front and rear parts 112a and 112b of the cleat 112 contact with the inner side faces of the cleat attachment section 164 in the lengthwise direction D3 of the cleat adjusting instrument 124 while the cleat 112 is attached to the cleat attachment section 164. Thus, the cleat 112 is fittedly attached to the cleat attachment section 164 without any plays in the lengthwise direction D3 of the cleat adjusting instrument 124. Moreover, as illustrated in FIG. 31, the front part 112a of the cleat 112 has a flange part 112c. The front edge portion of the cleat attachment section 164 has a step portion 164a defining a receiving space for the flange part 112c of the cleat 112, as best shown in FIGS. 29 and 30. Thus, the flange part 112c of the cleat 112 is engaged with the step portion 164a of the cleat attachment section 164 while the cleat 112 is attached to the cleat attachment section 164. As further illustrated in FIG. 29, the aperture 178 has a widthwise dimension D11 between left and right inner side faces of the cleat attachment section 164 that define the rear portion 178b of the aperture 178 therebetween. The widthwise dimension D11 of the aperture 178 is equal to or substantially equal to a widthwise dimension of the cleat 112 between leftmost and rightmost parts of the cleat 112. Outer side faces of the leftmost and rightmost parts of the cleat 112 contact with the inner side faces of the cleat attachment section 164 in the widthwise direction D4 of the cleat adjusting instrument 124 while the cleat 112 is attached to the cleat attachment section 164. Thus, the cleat 112 is fittedly attached to the cleat attachment section 164 without any plays in the widthwise direction D4 of the cleat adjusting instrument 124. The lengthwise and widthwise directions D3 and D4 are perpendicular to each other.

Referring to FIGS. 30 to 32, an attachment of the bicycle cleat positioning kit in accordance with the third embodiment will be further described in detail. First, the cleat 112 is temporarily and adjustably coupled to the shoe sole 116 of the bicycle shoe 114 with the cleat fasteners 118. When the cleat 112 is temporarily coupled to the shoe sole 116 of the bicycle shoe 114, the cleat fasteners 118 are not fully tightened to the threaded holes of the shoe sole 116. The cleat fasteners 118 are disposed through elongated holes of plate washers that are placed on recessed seats of the cleat 112, and threaded into the threaded holes of the shoe sole 116 of the bicycle shoe 114, as best shown in FIG. 31. Next, as best shown in FIG. 30, the cleat adjusting instrument 124 is set or attached to the cleat 112 such that the cleat 112 is disposed within the aperture 178 of the cleat attachment section 164 of the cleat adjusting instrument 124. In particular, the front part 112a and the flange part 112c of the cleat 112 are inserted into the front portion 178a of the aperture 178 of the cleat adjusting instrument 124, and then the cleat adjusting instrument 124 is pressed downward towards the shoe sole 116 of the bicycle shoe 114 such that the rear part 112b of the cleat 112 is inserted into the rear portion 178b of the aperture 178 of the cleat adjusting instrument 124 and the flange part 112c of the cleat 112 is engaged with the step portion 164a of the cleat attachment section 164. As a result, the cleat 112 is fittedly attached to the aperture 178 of the cleat adjusting instrument 124.

Furthermore, as best shown in FIG. 31, the reference indicating instrument 122 is attached to the bicycle shoe 114. In FIG. 31, the cleat adjusting instrument 124 attached to the cleat 112 is removed for better illustration of the attachment between the reference indicating instrument 122 and the bicycle shoe 114. As illustrated in FIG. 31, the projecting parts 152 of the shoe attachment section 134 of the reference indicating instrument 122 are inserted into the sockets 118a of the cleat fasteners 118, respectively. As a result, the reference indicating instrument 122 is non-movably attached to the bicycle shoe 114, but is relatively movable with respect to the cleat 112. At least a part of the reference indicating instrument 122 is overlaid on the cleat adjusting instrument 124 while the reference indicating instrument 122 is attached to the bicycle shoe 114 and the cleat adjusting instrument 124 is attached to the cleat 112. In particular, the shoe reference indicator 132 (see FIGS. 27 and 28) of the reference indicating instrument 122 is disposed on the cleat adjusting indicator 162 (see FIGS. 29 and 30) of the cleat adjusting instrument 124 while the reference indicating instrument 122 is overlaid on the cleat adjusting instrument 124. More specifically, as illustrated in FIG. 32, the longitudinal position reference line 140, the transverse position reference line 142 and the orientation reference lines 144 of the shoe reference indicator 132 of the reference indicating instrument 122 are disposed on the longitudinal adjustment scale 170, the transverse adjustment scale 172 and the orientation adjustment scales 174 of the cleat adjusting indicator 162 of the cleat adjusting instrument 124, respectively.

The longitudinal position reference line 140 and the longitudinal adjustment scale 170 are arranged on the reference indicating instrument 122 and the cleat adjusting instrument 124, respectively, such that the longitudinal position reference line 140 is aligned to the origin 170a of the longitudinal adjustment scale 170 when the cleat adjusting instrument 124 is aligned to the reference indicating instrument 122. Here, when the cleat adjusting instrument 124 is aligned to the reference indicating instrument 122, then the center point CP of the cleat 112 is aligned to a reference position of the reference indicating instrument 122 (or the shoe sole 116 of the bicycle shoe 114), and the lengthwise and widthwise directions D3 and D4 of the cleat adjusting instrument 124 are parallel to the lengthwise and widthwise directions D1 and D2 of the reference indicating instrument 122 (or the bicycle shoe 114), respectively. Furthermore, the transverse position reference line 142 and the transverse adjustment scale 172 are arranged on the reference indicating instrument 122 and the cleat adjusting instrument 124, respectively, such that the transverse position reference line 142 is aligned to the origin 172a of the transverse adjustment scale 172 when the cleat adjusting instrument 124 is aligned to the reference indicating instrument 122. Moreover, the orientation reference lines 144 and the orientation adjustment scales 174 are arranged on the reference indicating instrument 122 and the cleat adjusting instrument 124, respectively, such that the orientation reference lines 144 are aligned to the origins 174a of the orientation adjustment scales 174 when the cleat adjusting instrument 124 is aligned to the reference indicating instrument 122.

Referring now to FIGS. 32 to 36, an adjustment of the cleat 112 with respect to the bicycle shoe 114 using the bicycle cleat positioning kit in accordance with the third embodiment will be further described in detail. This bicycle cleat positioning kit in accordance with the third embodiment adjusts the cleat 112 with respect to the bicycle shoe 114 based on a plurality of parameter values obtained by the foot locating instrument 20 and the foot measuring instrument 22 through the bicycle cleat positioning method in accordance with the first embodiment. In particular, the bicycle cleat positioning kit adjusts the cleat 112 with respect to the bicycle shoe 114 based on the parameter values of the "SHOES-CLEAT ANGLE," the "F/R ADJUSTED POSITION," and the "NOMAL/LONG AXLE."

Figure 33:
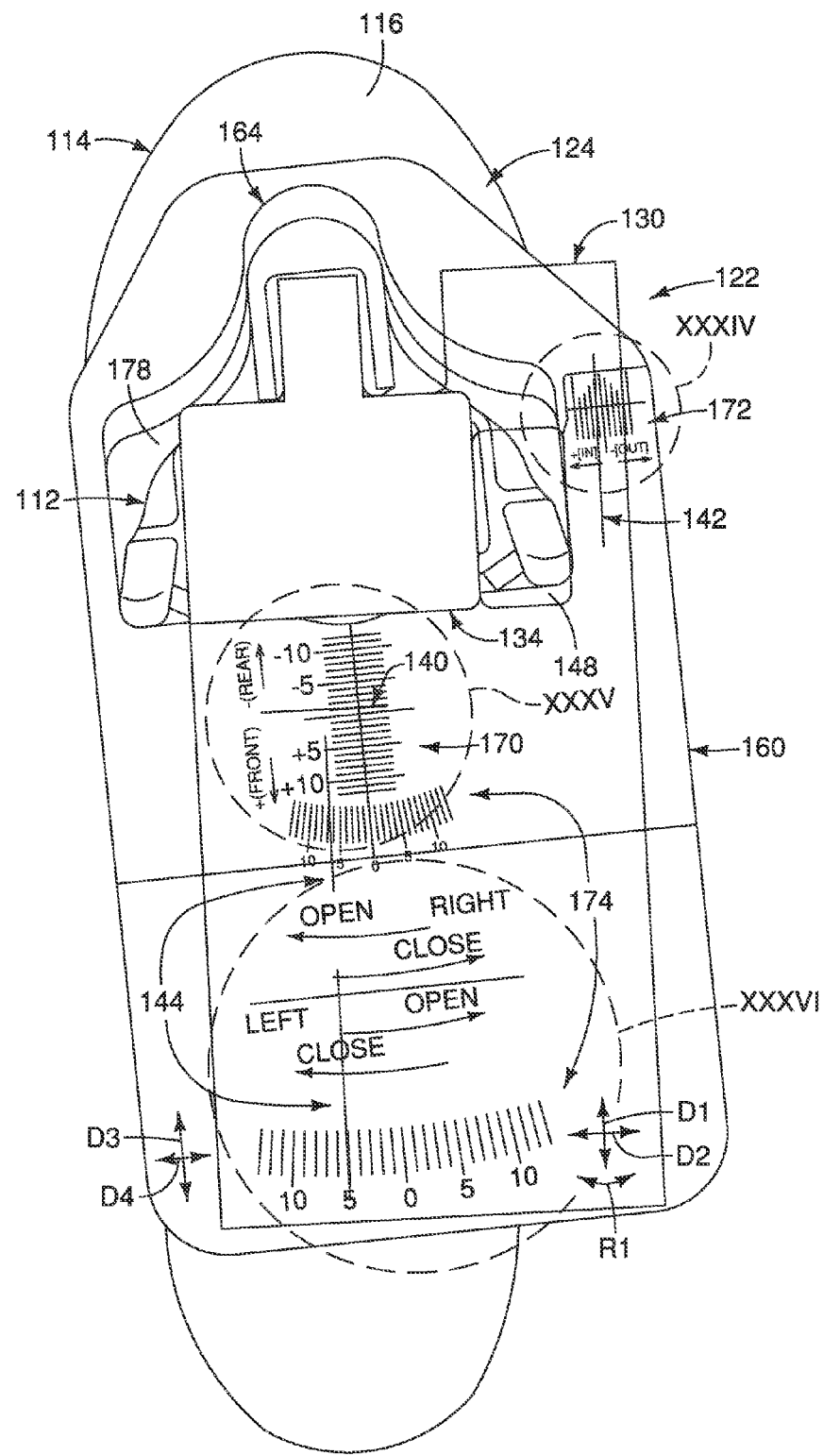
FIG. 33 is a top plan view of the reference indicating instrument illustrated in FIG. 27 and the cleat adjusting instrument illustrated in FIG. 29, illustrating the cleat adjusting instrument adjusted with respect to the reference indicating instrument.
Figure 35:
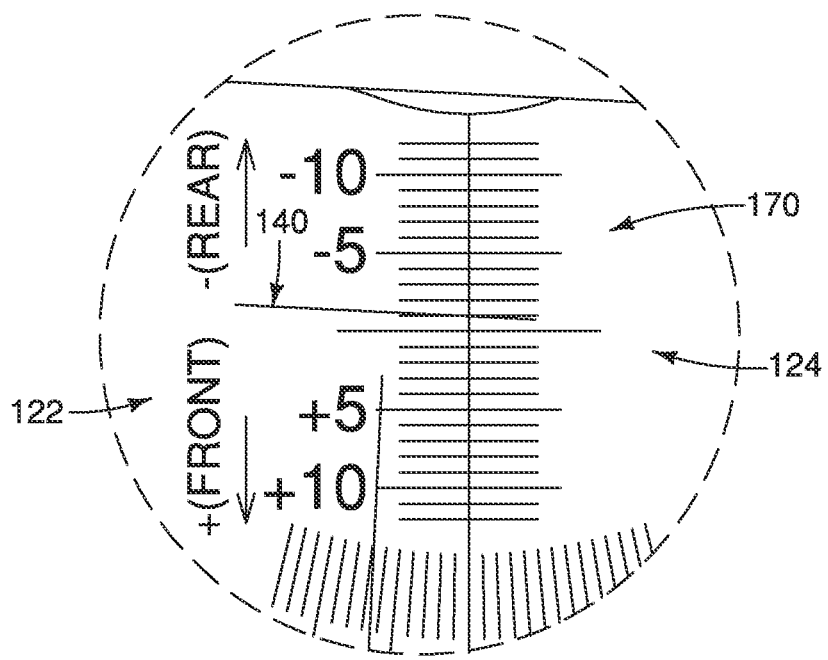
FIG. 35 is an enlarged top plan view of an encircled portion XXXV illustrated in FIG. 33, illustrating the cleat adjusting instrument adjusted with respect to the reference indicating instrument in a lengthwise direction.

In particular, the cleat adjusting instrument 124 is slidably adjusted relative to the reference indicating instrument 122 in the lengthwise direction D1 such that the longitudinal position reference line 140 is aligned to a line segment of the longitudinal adjustment scale 170 indicating the parameter value of the "F/R ADJUSTED POSITION." Specifically, if the longitudinal position reference line 140 is relatively adjusted with respect to the longitudinal adjustment scale 170 in the "+(FRONT)" direction by sliding the cleat adjusting instrument 124 relative to the reference indicating instrument 122 in the lengthwise direction D1, then the cleat 112 is adjusted forward relative to the bicycle shoe 114 towards a front most position of the cleat 112, which results in adjusting the bicycle shoe 114 rearward relative to a pedal axle of a bicycle pedal. On the other hand, if the longitudinal position reference line 140 is relatively adjusted with respect to the longitudinal adjustment scale 170 in the "−(REAR)" direction by sliding the cleat adjusting instrument 124 relative to the reference indicating instrument 122 in the lengthwise direction D1, then the cleat 112 is adjusted rearward relative to the bicycle shoe 114 towards a rear most position of the cleat 112, which results in adjusting the bicycle shoe 114 forward relative to the pedal axle of the bicycle pedal. For example, as illustrated in FIGS. 33 and 35, if the parameter value is "−1," then the cleat adjusting instrument 124 is slidably adjusted relative to the reference indicating instrument 122 in the lengthwise direction D1 such that the longitudinal position reference line 140 is disposed on a line segment of the longitudinal adjustment scale 170 indicating the parameter value "−1," which results in adjusting the cleat 112 rearward relative to the bicycle shoe 114 by 1 mm, and adjusting the bicycle shoe 114 forward relative to the pedal axle of the bicycle pedal by 1 mm.

Figure 34:
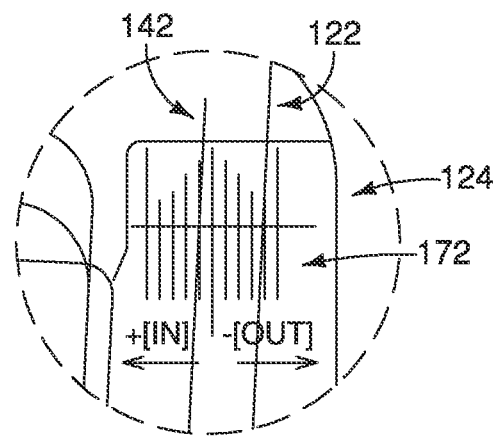
FIG. 34 is an enlarged top plan view of an encircled portion XXXIV illustrated in FIG. 33, illustrating the cleat adjusting instrument adjusted with respect to the reference indicating instrument in a widthwise direction.

Furthermore, the cleat adjusting instrument 124 is slidably adjusted relative to the reference indicating instrument 122 in the widthwise direction D2 such that the transverse position reference line 142 is aligned to a line segment of the transverse adjustment scale 172 indicating the parameter value of the "NOMAL/LONG AXLE." Specifically, if the transverse position reference line 142 is relatively adjusted with respect to the transverse adjustment scale 172 in the "+[IN]" direction by sliding the cleat adjusting instrument 124 relative to the reference indicating instrument 122 in the widthwise direction D2, then the cleat 112 is adjusted relative to the bicycle shoe 114 towards an outboard side of the bicycle shoe 114 for the left foot (or towards an inboard side of the bicycle shoe 114 for the right foot), which results in adjusting the bicycle shoe 114 for the left foot inwardly (or adjusting the bicycle shoe 114 for the right foot outwardly). On the other hand, if the transverse position reference line 142 is relatively adjusted with respect to the transverse adjustment scale 172 in the "−[OUT]" direction by sliding the cleat adjusting instrument 124 relative to the reference indicating instrument 122 in the widthwise direction D2, then the cleat 112 is adjusted relative to the bicycle shoe 114 towards the inboard side of the bicycle shoe 114 for the left foot (or towards the outboard side of the bicycle shoe 114 for the right foot), which results in adjusting the bicycle shoe 114 for the left foot outwardly (or adjusting the bicycle shoe 114 for the right foot inwardly). For example, as illustrated in FIGS. 33 and 34, if the parameter value is "+1," then the cleat adjusting instrument 124 is slidably adjusted relative to the reference indicating instrument 122 in the widthwise direction D2 such that the transverse position reference line 142 is disposed on a line segment of the transverse adjustment scale 172 indicating the parameter value "+1," which results in adjusting the cleat 112 outwardly by 1 mm relative to the bicycle shoe 114 for the left foot (or inwardly by 1 mm relative to the bicycle show 114 for the right foot). It should be understood from the drawings and the description herein that the term inboard side refers to the right side of a shoe for the left foot, and the left side of a shoe for the right foot. In other words the inboard side is the side of the shoe facing the shoe on the other foot of the wearer. Similarly, the term outboard side refers to the left side of the shoe for the left foot and the right side of the shoe for the right foot. The outboard side is the side of the shoe facing away from the shoe on the other foot.

Moreover, the cleat adjusting instrument 124 is rotatably adjusted relative to the reference indicating instrument 122 in the rotational direction R1 such that the orientation reference lines 144 are aligned to line segments of the orientation adjustment scales 174 indicating the parameter value of the "SHOES-CLEAT ANGLE." Specifically, if the orientation reference lines 144 are relatively adjusted with respect to the orientation adjustment scales 174 in the "OPEN" direction for the left foot (or the "CLOSE" direction for the right foot) by rotating the cleat adjusting instrument 124 relative to the reference indicating instrument 122 in the rotational direction R1, then the cleat 112 is adjusted relative to the bicycle shoe 114 such that the toe of the bicycle shoe 114 for the left foot is arranged farther from a center line of a bicycle frame than the heel of the bicycle shoe 114 for the left foot (i.e., "toe-out" or "open stance") (or such that the toe of the bicycle shoe 114 for the right foot is arranged closer to the center line of the bicycle frame than the heel of the bicycle shoe 114 for the left foot (i.e., "toe-in" or "closed stance")). On the other hand, if the orientation reference lines 144 are relatively adjusted with respect to the orientation adjustment scales 174 in the "CLOSE" direction for the left foot (or the "OPEN" direction for the right foot) by rotating the cleat adjusting instrument 124 relative to the reference indicating instrument 122 in the rotational direction R1, then the cleat 112 is adjusted relative to the bicycle shoe 114 such that the heel of the bicycle shoe 114 for the left foot is arranged farther from the center line of the bicycle frame than the toe of the bicycle shoe 114 for the right foot (i.e., "toe-in" or "closed stance") (or such that the heel of the bicycle shoe 114 for the right foot is arranged closer to the center line of the bicycle frame than the toe of the bicycle shoe 114 for the right foot (i.e., "toe-out" or "open stance")). For example, if the parameter value indicates that the cleat 112 should be rotated in the "CLOSE" direction for the left foot by 4.5 degree, then the cleat adjusting instrument 124 is rotatably adjusted relative to the reference indicating instrument 122 in the rotational direction R1 such that the orientation reference lines 144 is disposed on a line segment of the orientation adjustment scales 174 indicating the parameter value "4.5" in the "CLOSE" direction for the left foot, which results in setting the bicycle shoe 114 for the left foot to the toe-in when the bicycle shoe 114 is coupled to the bicycle pedal.

Figure 36:
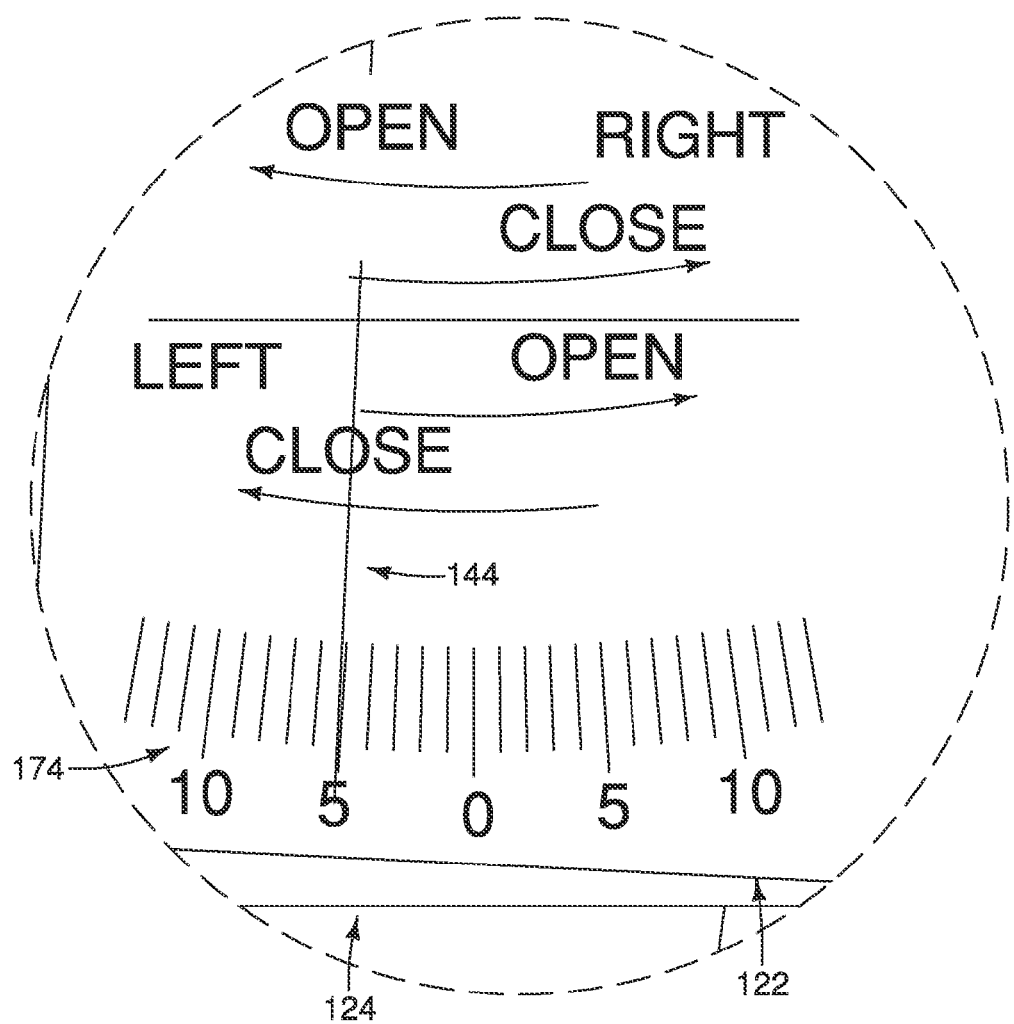
FIG. 36 is an enlarged top plan view of an encircled portion XXXVI illustrated in FIG. 33, illustrating the cleat adjusting instrument adjusted with respect to the reference indicating instrument in a rotational direction.

Alternatively or additionally, the cleat adjusting instrument 124 can be further rotatably adjusted relative to the reference indicating instrument 122 in the rotational direction R1 based on a widthwise adjustment of the cleat adjusting instrument 124 relative to the reference indicating instrument 122 in the widthwise direction D2 (e.g., based on the parameter value of the "NOMAL/LONG AXLE"). Specifically, the widthwise adjustment in the widthwise direction D2 affects a widthwise position of the orientation adjustment scales 174 relative to the orientation reference lines 144. Thus, if the transverse position reference line 142 is relatively adjusted with respect to the transverse adjustment scale 172 in the "+[IN]" direction, then the parameter value for the rotational adjustment in the clockwise direction (i.e., in the "CLOSE" direction for the left foot, or in the "OPEN" direction for the right foot) is corrected to decrease by 0.5 degree per 1 mm of the widthwise adjustment, and the parameter value for the rotational adjustment in the counterclockwise direction (i.e., in the "OPEN" direction for the left foot, or in the "CLOSE" direction for the right foot) is corrected to increase by 0.5 degree per 1 mm of the widthwise adjustment. On the other hand, if the transverse position reference line 142 is relatively adjusted with respect to the transverse adjustment scale 172 in the "−[OUT]" direction, then the parameter value for the rotational adjustment in the clockwise direction (i.e., in the "CLOSE" direction for the left foot, or in the "OPEN" direction for the right foot) is corrected to increase by 0.5 degree per 1 mm of the widthwise adjustment, and the parameter value for the rotational adjustment in the counterclockwise direction (i.e., in the "OPEN" direction for the left foot, or in the "CLOSE" direction for the right foot) is corrected to decrease by 0.5 degree per 1 mm of the widthwise adjustment. Then, the cleat adjusting instrument 124 is rotatably adjusted relative to the reference indicating instrument 122 in the rotational direction R1 such that the orientation reference lines 144 are aligned to line segments of the orientation adjustment scales 174 indicating the corrected parameter value. For example, if the parameter value for the rotational adjustment (e.g., the "SHOES-CLEAT ANGLE) indicates that the cleat 112 should be rotated in the "OPEN" direction for the left foot by "4.5" degree while the transverse position reference line 142 is relatively adjusted with respect to the transverse adjustment scale 172 in the "+[IN]" direction by 1 mm, as shown in FIG. 34, then the cleat adjusting instrument 124 is rotatably adjusted relative to the reference indicating instrument 122 in the rotational direction R1 such that the orientation reference lines 144 is disposed on a line segment of the orientation adjustment scales 174 indicating the corrected parameter value "5.0" in the "OPEN" direction for the left foot, as shown in FIGS. 33 and 36.

After adjusting the cleat 112 with respect to the shoe sole 116 of the bicycle shoe 114, the reference indicating instrument 122 is removed from the cleat fasteners 118 that have been temporarily fastened to the shoe sole 16 of the bicycle shoe 114. Then, the cleat fasteners 118 are fully tightened to the threaded holes of the shoe sole 16 of the bicycle shoe 114, thereby non-movably coupling the cleat 112 to the shoe sole 16 of the bicycle shoe 114.

In the illustrated embodiment, the bicycle cleat positioning kit adjusts the cleat 112 with respect to the bicycle shoe 114 based on the parameter values of the "SHOES-CLEAT ANGLE," the "F/R ADJUSTED POSITION," and the "NOMAL/LONG AXLE" in accordance with the first embodiment. However, the bicycle cleat positioning kit can utilize different parameter values for adjusting the cleat 112 with respect to the bicycle shoe 114 in the lengthwise, widthwise and rotational directions D1, D2 and R1. These parameter values can be obtained by conventional foot measurements conventionally used for cleat adjustment. Thus, detailed description of the parameter values will be omitted for the sake of brevity.

In the illustrated embodiment, the reference indicating instrument 122 is fixedly coupled to the bicycle shoe 114 by coupling the projecting parts 152 of the shoe attachment section 134 with the sockets 118*a* of the cleat fasteners 118. However, the reference indicating instrument 122 can be fixedly coupled to the bicycle shoe 114 in different manners. For example, the reference indicating instrument 122 can be fixedly coupled to the bicycle shoe 114 by coupling the projecting parts 152 with the threaded holes for the cleat fasteners 118, or by fixedly coupling a part of the reference indicating instrument 122 with a part of the bicycle shoe 114.

In the illustrated embodiment, the cleat 112 is adjusted with respect to the bicycle shoe 114 using the bicycle cleat positioning kit in accordance with the third embodiment. On the other hand, the bicycle cleat positioning kit in accordance with the third embodiment can also be used to measure the current positions and orientations of the cleat 112 with respect to the bicycle shoe 114. In this case, firstly, the cleat adjusting instrument 124 is attached to the cleat 112 that has been fixedly coupled to the bicycle shoe 114, and the reference indicating instrument 122 is coupled to the bicycle shoe 114. Then, displacements of the cleat 112 with respect to the bicycle shoe 114 are measured using the shoe reference indicator 132 of the reference indicating instrument 122 and the cleat adjusting indicator 162 of the cleat adjusting instrument 124. In particular, a lengthwise displacement of the cleat 112 is obtained as a location of the longitudinal position reference line 140 relative to the longitudinal adjustment scale 170, a widthwise displacement of the cleat 112 is obtained as a location of the transverse position reference line 142 relative to the transverse adjustment scale 172, and an orientation displacement of the cleat is obtained as a location of the orientation reference lines 144 relative to the orientation adjustment scales 174. After measuring the displacements of the cleat 112, the cleat 112 may be replaced with a new cleat. The new cleat is adjusted with respective to the bicycle shoe 114 in a manner described above using the measured displacement of the cleat 112 as the parameter values. With this arrangement, the cleat 112 can be easily replaced with the new cleat. In particular, the new cleat can be easily adjusted to the same position and orientation as the cleat 112.

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the selected embodiments according to the present invention are provided for illustration only, and not for the purpose of limiting the invention as defined by the appended claims and their equivalents.

What is claimed is:

1. A bicycle cleat positioning kit comprising:
    a reference indicating instrument including a shoe reference indicator with respect to a bicycle shoe; and
    a cleat adjusting instrument including a cleat adjusting indicator indicative of an adjustment amount of a cleat with respect to the shoe reference indicator of the reference indicating instrument,
    at least a part of the reference indicating instrument being overlaid on the cleat adjusting instrument while the reference indicating instrument is attached to the bicycle shoe and the cleat adjusting instrument is attached to the cleat.

2. The bicycle cleat positioning kit according to claim 1, wherein
    the reference indicating instrument further includes a shoe attachment section that is configured to be detachably coupled to the bicycle shoe.

3. The bicycle cleat positioning kit according to claim 2, wherein
    the shoe attachment section of the reference indicating instrument has an engagement structure that is configured to be engaged with a cleat fastener fastened to the bicycle shoe.

4. The bicycle cleat positioning kit according to claim 3, wherein
    the engagement structure has at least one projecting part that is configured to mate with a socket of the cleat fastener.

5. The bicycle cleat positioning kit according to claim 1, wherein
    the shoe reference indicator of the reference indicating instrument has at least one line part that represents one of a first reference position of the bicycle shoe in a first direction of the bicycle shoe, a second reference position of the bicycle shoe in a second direction of the bicycle shoe, and a reference orientation of the bicycle shoe.

6. The bicycle cleat positioning kit according to claim 5, wherein
    the first and second directions are perpendicular to each other.

7. The bicycle cleat positioning kit according to claim 1, wherein
    the cleat adjusting instrument further includes a cleat attachment section that is configured to be detachably coupled to the cleat.

8. The bicycle cleat positioning kit according to claim 7, wherein
    the cleat attachment section of the cleat adjusting instrument has an aperture within which the cleat is configured to be fittedly disposed.

9. The bicycle cleat positioning kit according to claim 8, wherein
    the cleat adjusting instrument is movable with the cleat with respect to the bicycle shoe while the cleat is adjustably coupled to the bicycle shoe.

10. The bicycle cleat positioning kit according to claim 1, wherein
    the cleat adjusting indicator of the cleat adjusting instrument has at least one scale part indicative of one of a first cleat position of the cleat relative to the bicycle shoe in a first direction of the bicycle shoe, a second cleat position of the cleat relative to the bicycle shoe in a second direction of the bicycle shoe, and a cleat orientation of the cleat relative to the bicycle shoe.

11. The bicycle cleat positioning kit according to claim 10, wherein
    the first and second directions are perpendicular to each other.

12. The bicycle cleat positioning kit according to claim 1, wherein
    the shoe reference indicator of the reference indicating instrument is disposed on the cleat adjusting indicator of the cleat adjusting instrument while the reference indicating instrument is overlaid on the cleat adjusting instrument.

13. The bicycle cleat positioning kit according to claim 1, wherein
the cleat adjusting instrument is movable with the cleat with respect to the bicycle shoe while the reference indicating instrument is stationary with respect to the bicycle shoe.

14. A bicycle cleat positioning kit comprising:
a reference indicating instrument including a shoe reference indicator with respect to a bicycle shoe and a transparent sheet member on which the shoe reference indicator is disposed; and
a cleat adjusting instrument including a cleat adjusting indicator indicative of an adjustment amount of a cleat with respect to the shoe reference indicator of the reference indicating instrument, the reference indicating instrument being disposed on top of the cleat adjusting instrument and being movably disposed with respect to the cleat adjusting instrument to locate the cleat adjustment indicator relative to the shoe reference indicator.

\* \* \* \* \*